US011746349B2

(12) United States Patent
Church et al.

(10) Patent No.: US 11,746,349 B2
(45) Date of Patent: Sep. 5, 2023

(54) DNA-GUIDED GENE EDITING AND REGULATION

(71) Applicant: President and Fellows of Harvard College, Cambridge, MA (US)

(72) Inventors: George M. Church, Brookline, MA (US); Luhan Yang, Somerville, MA (US); Margo R. Monroe, Boston, MA (US); Po-Yi Huang, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1385 days.

(21) Appl. No.: 16/076,022

(22) PCT Filed: Feb. 7, 2017

(86) PCT No.: PCT/US2017/016827
§ 371 (c)(1),
(2) Date: Aug. 7, 2018

(87) PCT Pub. No.: WO2017/139264
PCT Pub. Date: Aug. 17, 2017

(65) Prior Publication Data
US 2021/0189388 A1 Jun. 24, 2021

Related U.S. Application Data

(60) Provisional application No. 62/396,418, filed on Sep. 19, 2016, provisional application No. 62/292,962, filed on Feb. 9, 2016.

(51) Int. Cl.
| | |
|---|---|
| *C12N 15/113* | (2010.01) |
| *C12N 9/22* | (2006.01) |
| *C12N 9/96* | (2006.01) |
| *C12N 1/15* | (2006.01) |

(52) U.S. Cl.
CPC ............ *C12N 15/113* (2013.01); *C12N 9/22* (2013.01); *C12N 9/96* (2013.01); *C12Y 306/04013* (2013.01)

(58) Field of Classification Search
None
See application file for complete search history.

(56) References Cited

U.S. PATENT DOCUMENTS

| | | |
|---|---|---|
| 2009/0208534 A1 | 8/2009 | Xu et al. |
| 2014/0296503 A1 | 10/2014 | Avniel et al. |
| 2015/0089681 A1 | 3/2015 | Van Der Oost et al. |
| 2015/0110762 A1 | 4/2015 | Holmes et al. |
| 2015/0232881 A1 | 8/2015 | Glucksmann et al. |

FOREIGN PATENT DOCUMENTS

WO  WO-2014189628 A1 * 11/2014 ............ C12N 15/10

OTHER PUBLICATIONS

Swarts et al., The evolutionary journey of Argonaute proteins, Nat. Structure Mol. Biol. 21, 2014, 743-53. (Year: 2014).*
Cho et al., CRSPR engineering turns on genes, Nature 517, 2015, 560-62. (Year: 2015).*
Hutvagner, G. "Small RNA asymmetry in RNAi: Function in RISC assembly and gene regulation," FEBS Letters, Sep. 20, 2005 (Sep. 20, 2005), vol. 579, pp. 5850-5857.
Fu et al. "The prokaryotic Argonaute proteins enhance homology sequene-directed recombination in bacteria" Nucleic Acids Research; 2019; vol. 47; No. 7; pp. 3568-3579.
Lee et al. "NgAgo possesses guided DNA nicking activity" Nucleic Acids Research; 2021; vol. 49; No. 17; pp. 9926-9937.
Ryazansky et al. "The Expanded Universe of Prokaryotic Argonaute Proteins" Molecular Biology and Physiology; Nov./Dec. 2018; vol. 9; Issue 6; pp. e01935-18.
Kaya et al. "A bacterial Argonaute with noncanonical guide RNA specificity" PNAS; Apr. 12, 2016; vol. 113; No. 15; pp. 4057-4062.

* cited by examiner

*Primary Examiner* — Todd M Epstein
(74) *Attorney, Agent, or Firm* — Banner & Witcoff, Ltd.

(57) ABSTRACT

Methods and compositions of altering a eukaryotic cell are described including providing to the eukaryotic cell a guide DNA sequence complementary to a target nucleic acid sequence, providing to the eukaryotic cell an Ago enzyme or a nuclease null Ago protein that interacts with the guide DNA sequence for DNA-guided gene editing and regulation of the target nucleic acid sequence in a site specific manner.

18 Claims, 7 Drawing Sheets
Specification includes a Sequence Listing.

| dsDNA | /5Biosg/GTTTAATATCCAAAAGAAGTTTATGTCAAACATTTGAAAGAACAAAAACA |
| --- | --- |
| | TGTTTTTGTTCTTTCAAATGTTTGACATAAACTTCTTTTGGATATTAAAC |
| ssDNA | /5Biosg/GTTTAATATCCAAAAGAAGTTTATGTCAAACATTTGAAAGAACAAAAACA |
| siDNA | /5Phos/CAAATGTTTGACATAAACTT |
| n | /5Phos/CAGCCCTGGCTTGAACTGAG |

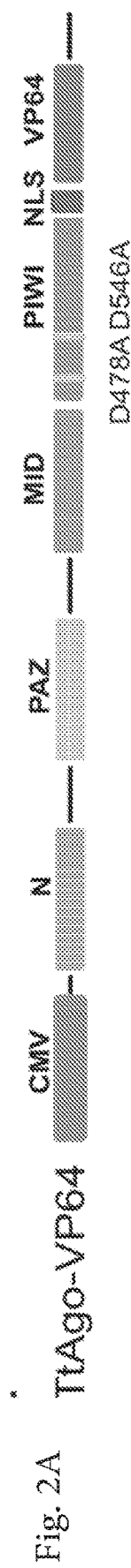
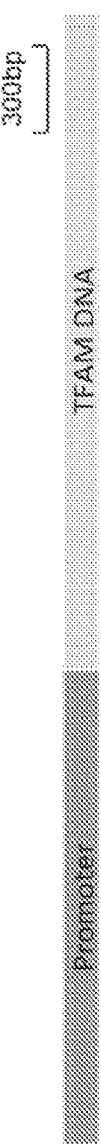
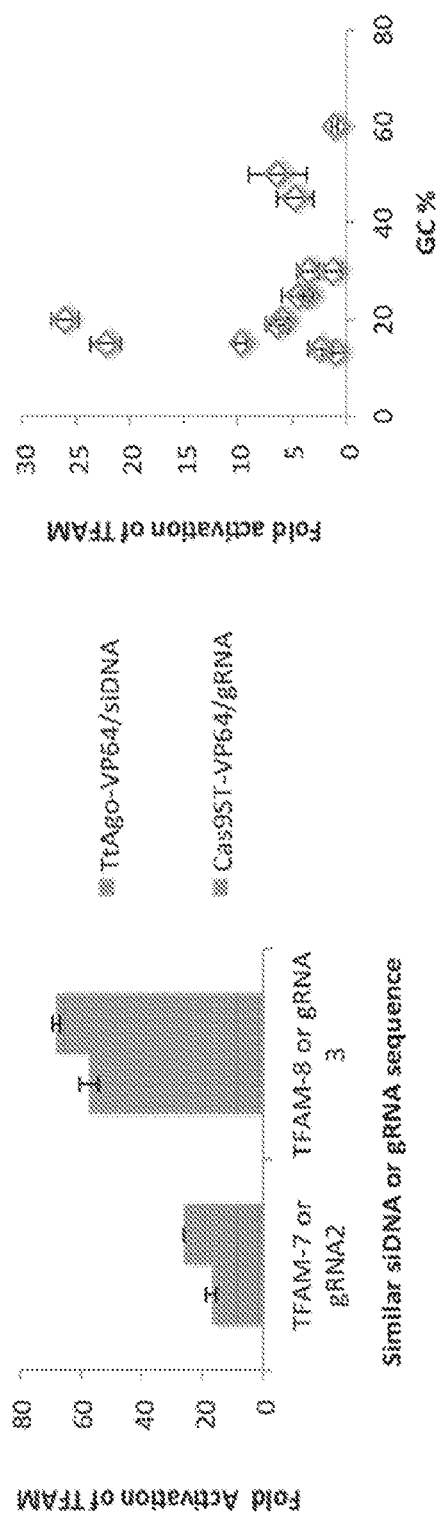
Fig. 2A
Fig. 2B
Fig. 2C
Fig. 2D $$Densitometry = \frac{\frac{I_{TtAgo-VP64/iDNA,TFAM}}{I_{TtAgo-VP64,TFAM}}}{\frac{I_{TtAgo-VP64/iDNA,Tubulin}}{I_{TtAgo-VP64,Tubulin}}}$$

```
                        SEQUENCE LISTING

<160> NUMBER OF SEQ ID NOS: 101

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgggaaggtc tggagca                                                        17

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccaagacag atgaaaacca c                                                   21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgtcttctg ctgagatgcc                                                     20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaagtgggtt gtttgccttt g                                                   21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagccaatct tcattgctca ag                                                  22

<210> SEQ ID NO 6
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
gaacaagtca tcctcattgc c                                              21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catgccaagc tctcgct                                                   17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatctcctca cgcagacg                                                  18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcctcactta caagacagct c                                              21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcctccaaga cctagccta                                                 19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttgactttgg ggttcaggtg                                                20

<210> SEQ ID NO 12
<211> LENGTH: 20
<212> TYPE: DNA
<213> ORGANISM: Artificial Sequence
<220> FEATURE:
```

<223> OTHER INFORMATION: Description of Artificial Sequence: Synthetic
    primer

<400> SEQUENCE: 12
gcgaacgtgg agaaagatgg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 13
ttcgggtagt ggaaaaccag                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 14
cagtagaaat acggctgcac                                               20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 15
gagactctgg catgctaact ag                                            22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 16
ggacatctaa gggcatcaca g                                             21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 17
tgaatgtgga agatgctgga                                               20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic

```
                                      primer

<400> SEQUENCE: 18
ttgccatgtg ccttgactt                                                19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aatccagtcc caggacatca                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtttggctg aataccttcc                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggagcttctc gacttcacca                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aacgccactg acaagaaagc                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
caaattattt tagaaatcaa                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 24
cagcggagcg tctcagttca                                                     20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagccctggc ttgaactgag                                                     20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagaaatagt aacgggagag                                                     20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cacggaatta agctctgcgg                                                     20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
catgttttat aaagtaatta                                                     20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tattaaactt tttgttgttt                                                     20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 30
caaaaagttt aatatccaaa                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
catggtatat aattacttta                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
catttgaaag aacaaaaaca                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
catttgtata aatcttgctg                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
caacttaaat gtaacttctg                                               20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
catgttttat aaagtaatta tat                                           23

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
```
caaaaagttt aatatccaaa a                                          21

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caaattattt tagaaatcaa cttaaat                                    27

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caattcctag agccatttgt c                                          21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cattttttct gcccaaaccc tt                                         22

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caagttctta gtagaatcca a                                          21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 cactttttt cactgttctg g                                           21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cagctacttt tgcattacaa t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caggttctgt tgctcggttt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cattcctgtt gaaccatatt c                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 ctaattttg tattttagt a                                                21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
caatagtctt agagtatcca                                                20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caaaggctat aaaaaaaatt a                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cagtttttct ctaatttatt c                                              21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
caagaaggta aaaacggct                                                      20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cataaaaaca gcgagggaga a                                                   21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
caggtattca acagagaaat t                                                   21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caatactctt ttcccctttc c                                                   21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caggaaaaca atgcatattt g                                                   21

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
catagaaaac acaattttaa aa                                                  22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 55
cagtttctga aagtaggaaa                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 56
catttcccac cctttctcga                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 57
catttctctt tgcaggttct                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 58
atttttgtct ccactctaac                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 59
ttcctccttc ttggttctgt                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 60
tcttcttttc ctcctttgtc                                              20

```
<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctcggagttc agaaatagta acggga                                              26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttaagctctg cggtaaggcc ttggaa                                              26

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acctaaaaat gcagattcca agg                                                 23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cgcctctccc gttactattt ggg                                                 23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
acacacggaa ttaagctctg cgg                                                 23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcgctaaaat gaagattaat ggg                                                 23

<210> SEQ ID NO 67
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttagaacttg ttaaattctg ggg                                            23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctacagaact aattagaaga                                                20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cttcctgatt caaagaaaaa                                                20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cttctttata tacctgccac                                                20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caacatgatg gagacggagc                                                20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
catgatgcag gaccagctgg                                                20

<210> SEQ ID NO 73
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cttcacatgt cccagcacta                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctctttctgt cctttcacga                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctacagacta ttccttgggg                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cttacaagtc ttctgccttt                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 ctttctccact ttcgccagcc                                             20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctttctgctg gcgccgcccg                                              20

<210> SEQ ID NO 79
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 79
cttcggtctc ttcgacgacg                                                 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctggattttt ttcgggtagt                                                 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctcaacgtta gcttcaccaa                                                 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cagccgtatt tctactgcga                                                 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cttgctttga agcatccgac                                                 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cttcacctat gcctgtgatt                                                 20

<210> SEQ ID NO 85
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 85
caaatgtctt ctgctgagat                                        20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
catttcacag aggaggacaa                                        20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctggaggaga aaccctggga                                        20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctttgacagc tttggcaacc                                        20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctcgccagtg aaatgatggc                                        20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caatgaggat gacttgttct                                        20

<210> SEQ ID NO 91
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 91
ctttgaagct gatggcccta                                                      20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctccccgctg ccgagccgtg                                                      20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ctgcgcagcc actaccgcga                                                      20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctttccgcgc gctggtggcc                                                      20

<210> SEQ ID NO 95
<211> LENGTH: 2256
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgaaccacc tgggtaaaac tgaagtattc ctgaaccgtt tcgcactgag accacttaat         60
ccggaagaac tgcgtccgtg gcgtctggaa gttgttctgg acccgccgcc gggtcgtgaa        120
gaagtttacc cgctgctggc tcaggttgct cgtcgtgctg gtgtgttac  cgttcgtatg        180 ggtgacggtc tggcttcttg gtctccgccg gaagtattag tacttgaagg taccctggct        240
cgtatgggtc agacctacgc atatcgttta tatccaaaag gtcgtcgtcc gctggatccg        300
aaggatcctg gtgaacgttc tgttctgtct gcattagcta gacgtctgct gcaggaacgt        360
ctgcgtcgtc tggaaggtgt ttgggttgaa ggtctggctg tttaccgtcg tgaacacgct        420
cgtggtccgg gttggcgtgt tctgggtggt gctgttctgg acctgtgggt ttctgactct        480
ggtgctttcc tgctggaagt tgacccggct taccgtatcc tgtgcgaaat gtctctggaa        540
gcttggctgg tcagggtca  cccgctgccg aaacgtgttc gtaacgctta cgaccgtcgt        600
acctgggaac tgctaagatt aggtgaagaa gacccgaaag aactgccgct gccgggtggt        660
```

```
ctgtctctgc tggactacca cgcttctaaa ggtcgtctgc agggtcgtga aggcgggaga      720
gtagcttggg ttgctgaccc gaaagacccg cgtaaaccga tcccgcacct gaccggtctg      780
ctggttccgg ttctgaccct ggaagacctg cacgaggaag aaggttctct ggctctgtct      840
ctgccgtggg aagaacgtcg tcgtcgtacc cgtgaaatcg cttcttggat cggtcgtcgt      900
ctgggtctgg gtaccccgga agctgttcgt gctcaggctt accgtctgtc tatcccgaaa      960
ctgatgggtc gtcgtgctgt ttctaaaccg gctgacgctc tgcgtgttgg tttctaccgt     1020
gctcaggaaa ccgcgttagc ccttttacga ctggacggtg ctcagggttg gccggaattc     1080
ctgcgtcggg ctctgctgcg tgctttcggt gcttctggtg cttctctgcg tctgcacacc     1140
ctgcacgctc acccgtctca gggtctggct ttccgtgaag ctctgcgtaa agctaaagaa     1200
gaaggtgttc aggctgttct ggttctgacc ccgccgatgg cttgggaaga ccgtaaccgt     1260
ctgaaagctc ttttactgag agagggcctg ccgagccaga tcctgaacgt tccgctgcgt     1320
gaagaagaac gtcaccgttg gaaaacgct ctgctgggtc tgctggctaa agctggtctg     1380
caggttgttg ctctgtctgg tgcttacccg gctgaactgg ctgttggttt cgccgctggt     1440
ggtcgtgaat ctttccgttt cggtggtgct gcttgcgctg ttggtggtga cggtggtcac     1500
ctgctgtgga ccctgccgga agctcaggct ggtgaacgta tcccgcagga agttgtttgg     1560
gacctgctgg aagaaaccct gtgggctttc cgtcgtaaag ctggtcgtct gccgtctcgt     1620
gttctgctgc tgcgtgccgg tcgtgttccg caggacgaat cgctctggc tttagaagcg     1680 ttagcgcgtg aaggtatcgc ttacgacctg gtttctgttc gtaaatctgg tggtggtcgt     1740
gtttacccgg ttcagggtcg tctggctgac ggtctgtacg ttccgctgga agacaaaacc     1800
ttcctgctgc tgaccgttca ccgtgacttc cgtggtaccc gcgtccgct gaaactggtt     1860 cacgaagctg gtgacacccc gctggaagct ctggctcacc agatcttcca cctgacccgt     1920
ctgtacccgg cttctggttt cgctttcccg gtctgccgg ctccgctgca cctggctgac     1980
cgtctggtta agaagttgg tcgtctgggt atccgtcacc tgaaagaagt tgaccgtgaa     2040
aaactgttct tcgttcccaa gaagaagaga aaggtggagg ccagcggttc cggacgggct     2100
gacgcattgg acgatttga tctggatatg ctgggaagtg acgccctcga tgattttgac     2160
cttgacatgc ttggttcgga tgcccttgat gactttgacc tcgacatgct cggcagtgac     2220
gcccttgatg atttcgacct ggacatgctg attaac                                2256
```

<210> SEQ ID NO 96
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
gtttaatatc caaagaagt ttatgtcaaa catttgaaag aacaaaaaca tgtttttgtt       60
ctttcaaatg tttgacataa acttcttttg gatattaaac                            100
```

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

```
gtttaatatc caaaagaagt ttatgtcaaa catttgaaag aacaaaaaca            50

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
caaatgtttg acataaactt                                             20

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tcaaattatt ttagaaatca a                                           21

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
caaattattc cagaaatcaa                                             20

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tcaaattatt ttagaaatca a                                           21
```

DNA-GUIDED GENE EDITING AND REGULATION

RELATED APPLICATIONS

This application is a National Stage Application under 35 U.S.C. 371 of PCT application PCT/US17/16827 designating the United States and filed Feb. 7, 2017; which claims the benefit of U.S. provisional application No. 62/396,418 and filed Sep. 19, 2016 and U.S. provisional application No. 62/292,962 and filed Feb. 9, 2016 each of which are hereby incorporated by reference in their entireties.

STATEMENT OF GOVERNMENT INTERESTS

This invention was made with government support under HG005550 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 7, 2017, is named 010498_00905-WO_SL.txt and is 26,801 bytes in size.

BACKGROUND

Argonaute (Ago) proteins, involved in RNA interference pathways, use small single-stranded RNA (ssRNA) to facilitate RNA interference of complementary ssRNA targets. See G. Meister, Argonaute proteins: functional insights and emerging roles. *Nature reviews. Genetics* 14, 447-459 (2013). Ago from *T. thermophiles* (TtAgo) was reported to prevent infection and propagation of foreign DNA by loading 5'-phosphorylated small interfering DNA (siDNA) guides approximately 20 base pairs (bp) in length to cut complementary single stranded DNA. See D. C. Swarts, M. M. Jore, E. R. Westra, Y. Zhu, J. H. Janssen, A. P. Snijders, Y. Wang, D. J. Patel, J. Berenguer, S. J. Brouns, J. van der Oost, DNA-guided DNA interference by a prokaryotic Argonaute. *Nature* 507, 258-261 (2014); G. Sheng, H. Zhao, J. Wang, Y. Rao, W. Tian, D. C. Swarts, J. van der Oost, D. J. Patel, Y. Wang, Structure-based cleavage mechanism of *Thermus thermophilus* Argonaute DNA guide strand-mediated DNA target cleavage. *Proc Natl Acad Sci USA* 111, 652-657 (2014); K. Nakanishi, D. E. Weinberg, D. P. Bartel, D. J. Patel, Structure of yeast Argonaute with guide RNA. *Nature* 486, 368-374 (2012); Y. Wang, S. Juranek, H. Li, G. Sheng, T. Tuschl, D. J. Patel, Structure of an argonaute silencing complex with a seed-containing guide DNA and target RNA duplex. Nature 456, 921-926 (2008).

SUMMARY

Aspects of the present disclosure are directed to a method of altering genomic nucleic acids in a eukaryotic cell using an Argonaute (Ago) protein and a guide DNA which form a complex with a target nucleic acid sequence. According to one aspect, an Ago system, i.e. one or more guide DNA and an Ago protein and/or alternatively a donor nucleic acid sequence, are provided to a eukaryotic cell to a target nucleic acid sequence. According to this aspect, the Ago system is used to cut or nick the target nucleic acid sequence or otherwise deliver a transcriptional regulator, such as a transcriptional activator or transcriptional repressor, to the target nucleic acid sequence, or otherwise insert the donor nucleic acid into the target nucleic acid sequence.

According to certain aspects, a method of modulating expression of a target nucleic acid sequence in a eukaryotic cell is provided including introducing into the cell a first foreign nucleic acid encoding one or more guide DNAs complementary to one or more target nucleic acids, introducing into the cell a second foreign nucleic acid encoding an Ago protein, such as an Ago enzyme, an Ago nuclease or a nuclease null Ago protein, introducing into the cell a third foreign nucleic acid encoding a transcriptional regulator protein or domain, wherein the Ago protein and the transcriptional regulator protein or domain are expressed, wherein the one or more guide DNAs, the Ago protein and the transcriptional regulator protein or domain co-localize to the target nucleic acid sequence and wherein the transcriptional regulator protein or domain regulates expression of the target nucleic acid sequence.

According to certain aspects, a method of integrating foreign DNA into a nucleic acid sequence of a eukaryotic cell is provided including providing to the cell a guide DNA sequence complementary to a target nucleic acid sequence, providing to the cell a donor sequence, providing to the cell an Ago enzyme that interacts with the guide DNA sequence and cleaves the target nucleic acid sequence in a site specific manner, wherein the guide DNA sequence binds to the complementary target nucleic acid sequence and the Ago enzyme cleaves the target nucleic acid sequence in a site specific manner; and wherein the donor sequence is integrated into the target nucleic acid sequence.

According to one aspect, the foreign nucleic acid encoding the Ago protein further encodes the transcriptional regulator protein or domain to create an expression product or fusion of the Ago protein attached to the transcriptional regulator protein or domain. According to this aspect, a third foreign nucleic acid encoding a transcriptional regulator or domain is not utilized. According to one aspect, the foreign nucleic acid further encodes a target of an RNA-binding domain and the foreign nucleic acid encoding the transcriptional regulator protein or domain further encodes an RNA-binding domain fused to the transcriptional regulator protein or domain. In this aspect, the guide DNA and the expressed transcriptional regulator protein or domain connect via the target of the RNA-binding domain and the RNA-binding domain. Other methods of linking a guide DNA and a transcriptional regulator protein or domain are known to those of skill in the art.

According to one aspect, the transcriptional regulator protein or domain is a transcriptional activator. According to one aspect, the transcriptional regulator protein or domain upregulates expression of the target nucleic acid sequence. According to one aspect, the transcriptional regulator protein or domain upregulates expression of the target nucleic acid sequence to treat a disease or detrimental condition. According to one aspect, the target nucleic acid sequence is associated with a disease or detrimental condition. According to one aspect, the transcriptional regulator protein or domain is a transcriptional repressor. According to one aspect, the transcriptional regulator protein or domain downregulates expression of the target nucleic acid sequence. According to one aspect, the transcriptional regulator protein or domain downregulates expression of the target nucleic acid sequence to treat a disease or detrimental condition. According to one aspect, the target nucleic acid sequence is associated with a disease or detrimental condition. According to one aspect, the transcriptional regulator or domain is a chromatin modifier, remodeller, or histone modifier including enzymes involved in histone acetylation, methylation, demethylation, phosphorylation, ubiquitination, sumoylation, ADP-ribosylation, deimination, and proline isomerization. According to one aspect, the transcriptional regulator protein or domain upregulates expression of the target nucleic acid sequence. According to one aspect, the transcriptional regulator protein or domain upregulates expression of the target nucleic acid sequence to treat a disease or detrimental condition.

According to one aspect of altering a target nucleic acid, two or more guide DNAs may be used with an Ago nuclease wherein the Ago nuclease co-localizes with the two or more guide DNAs to the target nucleic acid sequence and cuts the target nucleic acid sequence resulting in two or more adjacent cuts. According to one aspect, the two or more adjacent cuts are on the same strand of the double stranded target nucleic acid sequence. According to one aspect, the two or more adjacent cuts are on the same strand of the double stranded target nucleic acid sequence and result in homologous recombination. According to one aspect, the two or more adjacent cuts are on different strands of the double stranded target nucleic acid sequence. According to one aspect, the two or more adjacent cuts are on different strands of the double stranded target nucleic acid sequence and create double stranded breaks. According to one aspect, the two or more adjacent cuts are on different strands of the double stranded target nucleic acid sequence and create double stranded breaks resulting in nonhomologous end joining. According to one aspect, the two or more adjacent cuts are on different strands of the double stranded target nucleic acid sequence and are offset with respect to one another. According to one aspect, the two or more adjacent cuts are on different strands of the double stranded target nucleic acid sequence and are offset with respect to one another and create double stranded breaks. According to one aspect, the two or more adjacent cuts are on different strands of the double stranded target nucleic acid sequence and are offset with respect to one another and create double stranded breaks resulting in nonhomologous end joining.

According to one aspect, the two or more adjacent cuts are on different strands of the double stranded target nucleic acid and create double stranded breaks resulting in fragmentation of the target nucleic acid sequence thereby preventing expression of the target nucleic acid sequence.

According to one aspect, the method further includes introducing into the cell a third foreign nucleic acid encoding a donor nucleic acid sequence wherein the two or more cuts results in incorporation of the donor nucleic acid sequence into the target nucleic acid sequence through homologous recombination or nonhomologous end joining.

According to one aspect, a method of altering a eukaryotic cell is provided including the steps of providing to the eukaryotic cell a guide DNA sequence complementary to a target nucleic acid sequence, providing to the eukaryotic cell an Ago enzyme that interacts with the guide DNA sequence and cleaves the target nucleic acid sequence in a site specific manner, wherein the guide DNA sequence binds to the complementary target nucleic acid sequence and the Ago enzyme cleaves the target nucleic acid sequence in a site specific manner.

According to one aspect, methods described herein include providing a helicase to the cell where the helicase unwinds a helicase targeting target nucleic acid sequence. According to one aspect, methods described herein include providing a helicase to the cell where the helicase unwinds a helicase targeting target nucleic acid sequence where the helicase targeting nucleic acid sequence and the complementary target nucleic acid sequence are about 75 to 150 base pairs apart. According to one aspect, methods described herein include providing a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and the guide RNA targeting target nucleic acid sequence is unwound. According to one aspect, methods described herein include providing a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and the guide RNA targeting target nucleic acid sequence is unwound, and wherein the guide RNA targeting target nucleic acid sequence and the complementary target nucleic acid sequence are about 75 to 150 base pairs apart. According to one aspect, methods described herein include providing a donor sequence and wherein the donor sequence is inserted into the target nucleic acid sequence. According to one aspect, methods described herein include providing a plurality of guide DNAs into the cell that are complementary to different target nucleic acid sequences and the Ago enzyme cleaves the different target nucleic acid sequences in a site specific manner. According to methods described herein, the eukaryotic cell is a yeast cell, a plant cell, a mammalian cell or a human cell.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publications with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 2A to FIG. 2D are directed to engineered TtAgo$_{NN}$-VP64 activating human endogenous genes. FIG. 2A is a schematic depicting construction of TtAgo-VP64 having a CMV promoter driving an Ago double mutant D478A, D546A to remove nuclease activity fused with VP64 transcriptional domain with nuclear localization signal (NLS). FIG. 2B is a schematic of siDNA (guide DNA) targeted to TFAM promoter for activation of genomic locus. TFAM-7 and TFAM-8 were designed to target the promoter region of TFAM in the genome, 148 bp and 200 bp upstream of the transcriptional start site, respectively. FIG. 2C depicts data demonstrating that a TtAgo-VP64 system activates TFAM similarly to Cas9ST-VP64 system as measured by RT-QPCR of TFAM. FIG. 2D depicts data demonstrating that activation of endogenous genes decreases with the GC % of the 5'-phosphorylated 20 bp siDNA. A reverse correlation of GC % of siDNA targeting sequence with TtAgo-VP64/siDNA activation activities was observed.

DETAILED DESCRIPTION

Figure 1:
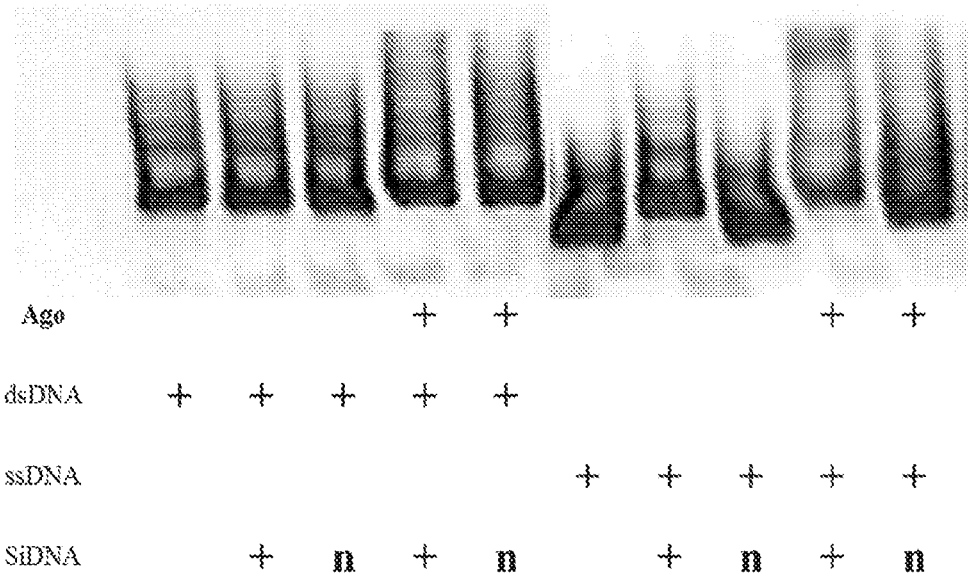
FIG. 1 depicts results of a gel shifting assay (SEQ ID NOS 96, 97, 98, and 25, respectively, in order of appearance).

Embodiments of the present disclosure are directed to methods of targeting one or more target nucleic acid sequences for editing or transcriptional regulation using an Ago protein and a guide DNA.

According to one aspect, an Ago system, i.e. an Ago enzyme and a guide DNA sequence, is provided to a eukaryotic cell. The guide DNA sequence and the Ago enzyme co-localize to the target nucleic acid sequence or otherwise co-localize with the target nucleic acid sequence, and the Ago cuts or cleaves the target nucleic acid sequence in a site specific manner. The Ago enzyme and the guide DNA sequence are referred to as a co-localization complex as that term is understood by one of skill in the art to the extent that the guide RNA and the Ago enzyme complex with a target nucleic acid sequence.

According to one aspect, an Ago system, i.e. an Ago enzyme and a guide DNA sequence, is provided to a eukaryotic cell. A donor nucleic acid sequence is also provided to the cell. The guide DNA sequence and the Ago enzyme co-localize to the target nucleic acid sequence or otherwise co-localize with the target nucleic acid sequence, and the Ago cuts or cleaves the target nucleic acid sequence in a site specific manner. The donor nucleic acid is inserted into the target nucleic acid sequence, such as by homologous recombination or non-homologous end joining. The Ago enzyme and the guide DNA sequence are referred to as a co-localization complex as that term is understood by one of skill in the art to the extent that the guide DNA sequence and the Ago enzyme complex with a target nucleic acid sequence.

According to one aspect, an Ago system, i.e. an Ago enzyme and a guide DNA sequence, is provided to a eukaryotic cell. A donor nucleic acid sequence is also provided to the cell, such as by being attached, connected or otherwise bound to either the Ago enzyme or the guide DNA sequence. The guide DNA sequence and the Ago enzyme co-localize to the target nucleic acid sequence or otherwise co-localize with the target nucleic acid sequence, and the Ago cuts or cleaves the target nucleic acid sequence in a site specific manner. The donor nucleic acid sequence is inserted into the target nucleic acid sequence, such as by homologous recombination or non-homologous end joining. The Ago enzyme and the guide DNA sequence are referred to as a co-localization complex as that term is understood by one of skill in the art to the extent that the guide DNA sequence and the Ago enzyme complex with a target nucleic acid sequence.

According to one aspect, an Ago system, i.e. a nuclease null Ago protein, i.e., an Ago protein that lacks enzymatic activity, and a guide DNA sequence, is provided to a eukaryotic cell. A transcriptional regulator is also provided to the cell. The guide DNA sequence and the nuclease null Ago protein co-localize to the target nucleic acid sequence or otherwise co-localize with the target nucleic acid sequence, and the transcriptional regulator regulates expression of the target nucleic acid sequence. The nuclease null Ago protein and the guide DNA sequence are referred to as a co-localization complex as that term is understood by one of skill in the art to the extent that the guide DNA sequence and the nuclease null Ago protein complex with a target nucleic acid sequence.

According to one aspect, an Ago system, i.e. an Ago nuclease and a guide DNA sequence, is provided to a eukaryotic cell. The guide DNA sequence and the Ago nuclease co-localize to the target nucleic acid sequence or otherwise co-localize with the target nucleic acid sequence, and the Ago nuclease cuts the target nucleic acid sequence in a site specific manner. According to one aspect, an Ago system, i.e. an Ago nuclease and a two or more guide DNA sequences, is provided to a eukaryotic cell. The guide DNA sequences and the Ago nuclease co-localize to target nucleic acid sequences at locations determined by the two guide DNA sequences or otherwise co-localize with the target nucleic acid sequences at locations determined by the two guide DNA sequences, and the Ago nuclease cuts the target nucleic acid at two adjacent sites. According to one aspect, a donor nucleic acid sequence may be provided which is inserted into the target nucleic acid sequence, such as by homologous recombination or non-homologous end joining. The Ago nuclease and the guide DNA sequence are referred to as a co-localization complex as that term is understood by one of skill in the art to the extent that the guide RNA and the Ago nuclease complex with a target nucleic acid.

According to one aspect, any of the methods using an Ago system described herein may also be used with a helicase. According to this aspect, the helicase is provided to the cell and may be used to unwind a target nucleic acid to facilitate the Ago system with cutting, nicking or delivering a transcriptional regulator to the target nucleic acid sequence. A suitable helicase is a nuclease null Cas9 protein. Such a nuclease null Cas9 protein can be used with a guide RNA to form a co-localization complex at or with a target nucleic acid sequence so as to unwind the target nucleic acid sequence into two separate single strand portions of the double stranded target nucleic acid. The unwound target nucleic acid sequence then facilitates co-localization of an Ago system at or near the target nucleic acid sequence.

According to one aspect, a eukaryotic cell is provided including a first nucleic acid sequence that is complementary to a target nucleic acid sequence, a second nucleic acid sequence encoding an Ago enzyme that interacts with the first nucleic acid sequence and cleaves the target nucleic acid sequence in a site specific manner, wherein the first nucleic acid sequence is a guide DNA, and wherein the cell expresses the Ago enzyme, and wherein the guide DNA binds to the complementary target nucleic acid and the Ago enzyme cleaves the target nucleic acid sequence in a site specific manner. In one embodiment, the eukaryotic cell is a yeast cell, a plant cell or a mammalian cell. In another embodiment, the eukaryotic cell is a human cell. In one embodiment, the eukaryotic cell further includes a plurality of nucleic acids encoding a plurality of guide DNA sequences complementary to different target nucleic acid sequences. In another embodiment, the eukaryotic cell of further comprises a helicase where the helicase unwinds a helicase targeting target nucleic acid sequence. In yet another embodiment, the eukaryotic cell further comprises a helicase where the helicase unwinds a helicase targeting target nucleic acid sequence where the helicase targeting nucleic acid sequence and the complementary target nucleic acid sequence are about 75 to 150 base pairs apart. In another embodiment, the eukaryotic cell further comprises a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence. In a further embodiment, the eukaryotic cell further comprises a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence, and wherein the guide RNA targeting target nucleic acid sequence and the complementary target nucleic acid sequence are about 75 to 150 base pairs apart. In another embodiment, the eukaryotic cell further comprises a donor sequence and wherein the donor sequence is inserted into the target nucleic acid sequence.

According to another aspect, a eukaryotic cell is provided including a first nucleic acid sequence that is complementary to a target nucleic acid sequence, a second nucleic acid sequence encoding a nuclease null Ago protein, wherein the nuclease null Ago protein includes a transcriptional regulator domain connected thereto for modulating target nucleic acid expression, wherein the guide DNA and the nuclease null Ago protein including the transcriptional regulator domain co-localize at the target nucleic acid sequence and wherein the transcriptional regulator domain modulates expression of the target nucleic acid sequence. In one embodiment, the eukaryotic cell further comprises a helicase where the helicase unwinds a helicase targeting target nucleic acid sequence. In another embodiment, the eukaryotic cell further comprises a helicase where the helicase unwinds a helicase targeting target nucleic acid sequence where the helicase targeting nucleic acid sequence and the complementary target nucleic acid sequence are about 75 to 150 base pairs apart. In one embodiment, the eukaryotic cell further comprises a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence. In another embodiment, the eukaryotic cell further comprises a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence, and wherein the guide RNA targeting target nucleic acid sequence and the complementary target nucleic acid sequence are about 75 to 150 base pairs apart. In one embodiment, the transcriptional regulator is a transcriptional activator or a transcriptional repressor. In another embodiment, the eukaryotic cell further comprises a plurality of guide DNAs that are complementary to different target nucleic acid sequences and the nuclease null Ago protein modulates expression of the different target nucleic acid sequences in a site specific manner. In one embodiment, the eukaryotic cell is a yeast cell, a plant cell or a mammalian cell. In another embodiment, the eukaryotic cell is a human cell.

According to one aspect, one or more vectors are used to introduce one or more nucleic acids encoding an Ago system, i.e. an Ago protein and a guide DNA sequence, and optionally a donor nucleic acid sequence, into a eukaryotic cell for editing or transcriptional regulation. A transcriptional regulator may be provided to the cell separately or may be attached, connected or otherwise bound to either the Ago protein or the guide DNA for delivery to the target nucleic acid sequence to be regulated. The nucleic acids are expressed and the Ago system cuts or nicks the target nucleic acid sequence or otherwise delivers a transcriptional regulator to the target nucleic acid sequence. Together, a guide DNA and an Ago protein are referred to as a co-localization complex as that term is understood by one of skill in the art to the extent that the guide DNA sequence and the Ago protein complex with a target nucleic acid sequence. According to certain aspects, a vector may include one or more nucleic acids encoding an Ago protein, a guide DNA, a donor nucleic acid sequence and/or a transcriptional regulator. The vectors may include any additional genetic regulatory elements as known to those of skill in the art, such as regulators, promoters, nuclear localization signals (NLS), start codons, stop codons, a transgene etc. According to certain aspects, one or more nucleic acids encoding an Ago protein, a guide DNA sequence, a donor nucleic acid sequence and/or a transcriptional regulator may be present within the same vector or present within different vectors.

Vectors according to the present disclosure include those known in the art as being useful in delivering genetic material into a cell and would include regulators, promoters, nuclear localization signals (NLS), start codons, stop codons, a transgene etc., and any other genetic elements useful for integration and expression, as are known to those of skill in the art.

AGO Description

Argonaute (Ago) proteins, involved in RNA interference pathways, use small single-stranded RNA (ssRNA) to facilitate RNA interference of complementary ssRNA targets. See G. Meister, Argonaute proteins: functional insights and emerging roles. *Nature reviews. Genetics* 14, 447-459 (2013). Ago from *T. thermophiles* (TtAgo) was reported to prevent infection and propagation of foreign DNA by loading 5'-phosphorylated small interfering DNA (siDNA) guides approximately 20 base pairs (bp) in length to cut complementary single stranded DNA. See D. C. Swarts, M. M. Jore, E. R. Westra, Y. Zhu, J. H. Janssen, A. P. Snijders, Y. Wang, D. J. Patel, J. Berenguer, S. J. Brouns, J. van der Oost, DNA-guided DNA interference by a prokaryotic Argonaute. *Nature* 507, 258-261 (2014); G. Sheng, H. Zhao, J. Wang, Y. Rao, W. Tian, D. C. Swarts, J. van der Oost, D. J. Patel, Y. Wang, Structure-based cleavage mechanism of

*Thermus thermophilus* Argonaute DNA guide strand-mediated DNA target cleavage. *Proc Natl Acad Sci USA* 111, 652-657 (2014); K. Nakanishi, D. E. Weinberg, D. P. Bartel, D. J. Patel, Structure of yeast Argonaute with guide RNA. *Nature* 486, 368-374 (2012); Y. Wang, S. Juranek, H. Li, G. Sheng, T. Tuschl, D. J. Patel, Structure of an argonaute silencing complex with a seed-containing guide DNA and target RNA duplex. *Nature* 456, 921-926 (2008).

An exemplary Ago protein is Ago from *Thermus thermophiles* (TtAgo) or a modification or homolog thereof. Sequences of Ago protein species are known to those of skill in the art. According to one aspect, the Ago enzyme, or the nuclease null Ago includes homologs and orthologs thereof and which retain the ability of the protein to bind to the DNA and be guided by the guide DNA sequence. According to one aspect, the Ago protein includes the sequence as known for naturally occurring *Thermus thermophiles* Ago and protein sequences having at least 30%, 40%, 50%, 60%, 70%, 80%, 90%, 95%, 98% or 99% homology thereto and being a DNA binding protein. According to one aspect, the Ago protein includes protein sequences having at least 10%, 20%, 30%, 40%, 50%, 60%, 70%, 80%, 90%, 95%, 98% or 99% homology to the naturally occurring *Thermus thermophiles* Ago and being a DNA binding protein. An exemplary Ago protein is Ago from haloalkaliphilic archaebacterium *N. gregoryi* SP2 (NgAgo) or a modification or homolog thereof. A non-exhaustive list of protein sequences that have been identified as relevant Ago proteins by searching the public databases such as (NCBI, GENBANK and UniProt) with the TtAgo sequence is provided below.

| UniProt Sequence Entry Name | UniProt Submitted Name | Organism | |
|---|---|---|---|
| Q53W94_THET8 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/JCM 8422/Vc1) | 0.00E+00 |
| K9XZC6_STAC7 | Stem cell self-renewal protein Piwi | Stanieria cyanosphaera (strain ATCC 29371/PCC 7437) | 7.60E−60 |
| B1XJG0_SYNP2 | Uncharacterized protein | Synechococcus sp. (strain ATCC 27264/PCC 7002/PR-6) | 1.30E−58 |
| A0A0C1VHB4_9CYAN | Uncharacterized protein | Lyngbya confervoides BDU141951 | 1.60E−58 |
| E0UCX3_CYAP2 | Stem cell self-renewal protein Piwi domain protein | Cyanothece sp. (strain PCC 7822) | 1.60E−55 |
| Q2JI93_SYNJB | Piwi domain protein | Synechococcus sp. (strain JA-2-3B'a(2-13)) | 2.30E−45 |
| Q8DKB1_THEEB | Tll0948 protein | Thermosynechococcus elongatus (strain BP-1) | 3.50E−44 |
| Q31N05_SYNE7 | Uncharacterized protein | Synechococcus elongatus (strain PCC 7942) | 1.30E−42 |
| D3S0S6_FERPA | Stem cell self-renewal protein Piwi domain protein | Ferroglobus placidus (strain DSM 10642/AEDII12DO) | 1.60E−40 |
| Y1321_METJA | Uncharacterized protein MJ1321 | Methanocaldococcus jannaschii (strain ATCC 43067/DSM 2661/JAL-1/JCM 10045/NBRC 100440) | 1.50E−35 |
| I3TE64_THEC1 | Uncharacterized protein | Thermogladius cellulolyticus (strain 1633) | 2.70E−30 |
| Q5P0R2_AROAE | Uncharacterized protein | Aromatoleum aromaticum (strain EbN1) | 9.10E−22 |
| L0JS08_NATP1 | Uncharacterized protein | Natrinema pellirubrum (strain DSM 15624/JCM 10476/NCIMB 786) | 2.60E−21 |
| R5NJJ8_9FIRM | Uncharacterized protein | Eubacterium sp. CAG: 603 | 3.40E−21 |
| R7RTW6_9CLOT | Uncharacterized protein | Thermobrachium celere DSM 8682 | 1.50E−19 |
| R5XQK4_9CLOT | Piwi domain protein | Clostridium bartlettii CAG: 1329 | 1.50E−19 |
| F8D8G0_HALXS | Stem cell self-renewal protein Piwi | Halopiger xanaduensis (strain DSM 18323/JCM 14033/SH-6) | 1.20E−18 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |
| E0UCX3_CYAP3 | Stem cell self-renewal protein Piwi domain protein | Cyanothece sp. (strain PCC 7822) | 0.00E+00 |
| Q2JI93_SYNJB | Piwi domain protein | Synechococcus sp. (strain JA-2-3B'a(2-13)) | 0.00E+00 |
| Q8DKB1_THEEB | Tll0948 protein | Thermosynechococcus elongatus (strain BP-1) | 0.00E+00 |

-continued

| UniProt Sequence Entry Name | UniProt Submitted Name | Organism | |
|---|---|---|---|
| Q31N05_SYNE8 | Uncharacterized protein | Synechococcus elongatus (strain PCC 7942) | 0.00E+00 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |
| E0UCX3_CYAP3 | Stem cell self-renewal protein Piwi domain protein | Cyanothece sp. (strain PCC 7822) | 0.00E+00 |
| Q2JI93_SYNJB | Piwi domain protein | Synechococcus sp. (strain JA-2-3B'a(2-13)) | 0.00E+00 |
| Q8DKB1_THEEB | TII0948 protein | Thermosynechococcus elongatus (strain BP-1) | 0.00E+00 |
| Q31N05_SYNE8 | Uncharacterized protein | Synechococcus elongatus (strain PCC 7942) | 0.00E+00 |
| D3S0S6_FERPA | Stem cell self-renewal protein Piwi domain protein | Ferroglobus placidus (strain DSM 10642/AEDII12DO) | 0.00E+00 |
| Y1321_METJA | Uncharacterized protein MJ1322 | Methanocaldococcus jannaschii (strain ATCC 43067/DSM 2661/JAL-1/JCM 10045/NBRC 100440) | 0.00E+00 |
| I3TE64_THEC2 | Uncharacterized protein | Thermogladius cellulolyticus (strain 1633) | 0.00E+00 |
| Q5P0R2_AROAE | Uncharacterized protein | Aromatoleum aromaticum (strain EbN1) | 0.00E+00 |
| L0JS08_NATP2 | Uncharacterized protein | Natrinema pellirubrum (strain DSM 15624/JCM 10476/NCIMB 786) | 0.00E+00 |
| R5NJJ8_9FIRM | Uncharacterized protein | Eubacterium sp. CAG: 604 | 0.00E+00 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |
| E0UCX3_CYAP3 | Stem cell self-renewal protein Piwi domain protein | Cyanothece sp. (strain PCC 7822) | 0.00E+00 |
| Q2JI93_SYNJB | Piwi domain protein | Synechococcus sp. (strain JA-2-3B'a(2-13)) | 0.00E+00 |
| Q8DKB1_THEEB | TII0948 protein | Thermosynechococcus elongatus (strain BP-1) | 0.00E+00 |
| Q31N05_SYNE8 | Uncharacterized protein | Synechococcus elongatus (strain PCC 7942) | 0.00E+00 |
| D3S0S6_FERPA | Stem cell self-renewal protein Piwi domain protein | Ferroglobus placidus (strain DSM 10642/AEDII12DO) | 0.00E+00 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |
| E0UCX3_CYAP3 | Stem cell self-renewal protein Piwi domain protein | Cyanothece sp. (strain PCC 7822) | 0.00E+00 |
| Q2JI93_SYNJB | Piwi domain protein | Synechococcus sp. (strain JA-2-3B'a(2-13)) | 0.00E+00 |
| Q8DKB1_THEEB | TII0948 protein | Thermosynechococcus elongatus (strain BP-1) | 0.00E+00 |

-continued

| UniProt Sequence Entry Name | UniProt Submitted Name | Organism | |
|---|---|---|---|
| Q31N05_SYNE8 | Uncharacterized protein | Synechococcus elongatus (strain PCC 7942) | 0.00E+00 |
| D3S0S6_FERPA | Stem cell self-renewal protein Piwi domain protein | Ferroglobus placidus (strain DSM 10642/AEDII12DO) | 0.00E+00 |
| Y1321_METJA | Uncharacterized protein MJ1322 | Methanocaldococcus jannaschii (strain ATCC 43067/ DSM 2661/JAL-1/JCM 10045/NBRC 100440) | 0.00E+00 |
| I3TE64_THEC2 | Uncharacterized protein | Thermogladius cellulolyticus (strain 1633) | 0.00E+00 |
| Q5P0R2_AROAE | Uncharacterized protein | Aromatoleum aromaticum (strain EbN1) | 0.00E+00 |
| L0JS08_NATP2 | Uncharacterized protein | Natrinema pellirubrum (strain DSM 15624/JCM 10476/ NCIMB 786) | 0.00E+00 |
| R5NJJ8_9FIRM | Uncharacterized protein | Eubacterium sp. CAG: 604 | 0.00E+00 |
| R7RTW6_9CLOT | Uncharacterized protein | Thermobrachium celere DSM 8683 | 0.00E+00 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/ JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |
| Q53W94_THET9 | Uncharacterized protein | Thermus thermophilus (strain HB8/ATCC 27634/DSM 579) | 0.00E+00 |
| Q8U3D2_PYRFU | Uncharacterized protein | Pyrococcus furiosus (strain ATCC 43587/DSM 3638/ JCM 8422/Vc1) | 0.00E+00 |
| K9XZC6_STAC8 | Stem cell self-renewal protein Piwi | Stanieria cyanosphaera (strain ATCC 29371/PCC 7437) | 0.00E+00 |
| B1XJG0_SYNP3 | Uncharacterized protein | Synechococcus sp. (strain ATCC 27264/PCC 7002/PR-6) | 0.00E+00 |
| A0A0C1VHB4_9CYAN | Uncharacterized protein | Lyngbya confervoides BDU141952 | 0.00E+00 |

It is well known in the art that eukaryotic Argonaute proteins are involved in small RNA-mediated silencing mechanisms such as RNA interference (RNAi), microRNA repression and piRNA-mediated transposon silencing. Argonautes bind small RNAs that guide them to RNA targets in order to regulate gene expression and repress invasive genomic elements. Carthew R W, Sontheimer E J., Origins and Mechanisms of miRNAs and siRNAs, *Cell*. Vol. 136, Pp 642-655, (2009). Prokaryotic Argonaute proteins are found in many bacterial and archaeal species and are well documented in the art. Exemplary prokaryotic Argonaute proteins described in the following references including supplementary information are hereby incorporated by reference in their entireties. For example, bioinformatics analysis and the phylogenetic distribution of Argonaute proteins in bacteria and archaea indicate that about 20% of sequenced strains contain at least one Ago gene. Makarova K S, et al., Prokaryotic homologs of Argonaute proteins are predicted to function as key components of a novel system of defense against mobile genetic elements. *Biology direct.* 4:29, (2009). Molloy S, Bacterial argonaute sets sail, *Nature Reviews Microbiology*, Vol. 11, Pp 743, (2013). Bacterial *Aquifex aeolicus* and archaeal *Pyrococcus furiosus* Ago proteins have also been reported and well known, e.g., via structural studies. Song J J, et al., Crystal structure of Argonaute and its implications for RISC slicer activity, *Science*, Vol. 305, Pp 1434-1437, (2004). Yuan Y R, et al., Crystal structure of A. aeolicus argonaute, a site-specific DNA-guided endoribonuclease, provides insights into RISC-mediated mRNA cleavage, *Mol Cell.*, *Vol.* 19, Pp 405-419, (2005). It has been known in the art that several prokaryotic Agos, unlike their eukaryotic counterparts, bind single-stranded DNA guides in vitro for cleavage of RNA targets. The presence of an Ago gene correlated with other known genome protection systems suggests roles of prokaryotic Agos for protecting cells from invasive nucleic acids.

Argonautes have also been known in the gram-negative bacteria *Rhodobacter sphaeroides* (RsAgo) and *Thermus thermophilus* (TtAgo). Olovnikov I, et al., Bacterial argonaute samples the transcriptome to identify foreign DNA, *Molecular cell.*, Vol. 51, Pp: 594-605, (2013). Swarts D C, et al. DNA-guided DNA interference by a prokaryotic Argonaute, Nature, Vol. 507, Pp: 258-261, (2014). These Agos from both bacterial species directly target DNA molecules and protect the genome against foreign and possibly invasive genomic elements, such as plasmids. However, there are important differences between Agos from both bacterial species in that RsAgo uses small RNAs as guide molecules, whereas TtAgo uses small DNAs as guide molecules. The Ago 5' binding pocket discriminates its guide by the nature of the first nucleotide. For example, in *Rhodo*-

*bacter sphaeroides*, there is a strong nucleotide bias for uridine at the 5' position for RsAgo-associated small RNA guide molecules. Whereas in *Thermus thermophiles*, there is a strong nucleotide bias for deoxycytidine at the 5' position for TtAgo-associated small DNA guide molecules. In the case of TtAgo, its endonuclease activity cleaves DNA targets in the middle of the region targeted by the guide DNA. Unlike the CRISPR-Cas system, which is another prokaryotic genomic host defense system, where effector proteins associate with host-encoded RNA guides to determine DNA cleavage loci, the Agos in both bacteria *Rhodobacter sphaeroides* and *Thermus thermophilus* recognize properties inherent to invading DNAs and silence them without using small RNA or DNA guides encoded in separate genomic loci. Hur, J K., et al., Prokaryotic Argonautes defend genomes against invasive DNA, *Trends Biochem Sci.*, June, Vol. 39(6): 257-259, (2014), Wiedenheft B, et al., RNA-guided genetic silencing systems in bacteria and archaea, *Nature*, Vol. 482, Pp 331-338, (2012).

According to certain aspects, an Ago enzyme is altered or otherwise modified to inactivate the nuclease activity. Such alteration or modification includes altering one or more amino acids to inactivate the nuclease activity or the nuclease domain. For example, modifications at D478A and D546A result in a nuclease null Ago protein. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the Ago protein. Other modifications to inactivate nuclease activity will be readily apparent to one of skill in the art based on the present disclosure. The nuclease-null Ago protein retains the ability to bind to DNA even though the nuclease activity has been inactivated. Accordingly, the nuclease null Ago protein includes the polypeptide sequence or sequences required for DNA binding but may lack the one or more or all of the nuclease sequences exhibiting nuclease activity or may be altered to render the nuclease sequences inactive.

According to certain aspects, the Ago protein may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to one aspect, the Ago protein is exogenous to the cell. According to one aspect, the Ago protein is foreign to the cell. According to one aspect, the Ago protein is non-naturally occurring within the cell.

According to one aspect, the nucleic acid sequence encoding the TtAgo protein or its variants is codon optimized for optimal host cell expression. In one embodiment, the nucleic acid sequence encoding the TtAgo protein or its variants is codon optimized for human cell expression.

CAS9 Helicase Description

Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus*. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: Methanococcus maripaludis C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; Persephonella marina EX H1; *Bacteroides fragilis* NCTC 9434; Capnocytophaga ochracea DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma mobile* 163K; *Mycoplasma penetrans; Mycoplasma synoviae* 53; *Streptobacillus moniliformis* DSM 12112; *Bradyrhizobium* BTAi 1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis holarctica; Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, Cas9 is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein, such as a nuclease null Cas9 protein, includes polypeptide sequences modified to inactivate nuclease activity or removal of a polypeptide sequence or sequences to inactivate nuclease activity. The nuclease-null Cas9 retains the ability to bind to DNA even though the nuclease activity has been inactivated. Accordingly, the nuclease null Cas9 includes the polypeptide sequence or sequences required for DNA binding but may lack the one or more or all of the nuclease sequences exhibiting nuclease activity.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc")

and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. Cell 154, 442-451 (2013); *Mali*, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. Cell 157, 1262-1278 (2014); Chen, B. et al. Dynamic imaging of genomic loci in living human cells by an optimized CRISPR/Cas system. Cell 155, 1479-1491 (2013); Shalem, O. et al. Genome-scale CRISPR-Cas9 knockout screening in human cells. Science 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. Cell (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

According to certain aspects, the helicase, such as a nuclease null Cas9, may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to one aspect, the Cas9 protein is exogenous to the cell. According to one aspect, the Cas9 protein is foreign to the cell. According to one aspect, the Cas9 protein is non-naturally occurring within the cell.

Guide DNA Description

Embodiments of the present disclosure are directed to the use of an Ago system and, in particular, a guide DNA which includes a spacer sequence. The term spacer sequence is understood by those of skill in the art and may include any polynucleotide having sufficient complementarity with a target nucleic acid sequence to hybridize with the target nucleic acid sequence and direct sequence-specific binding of an Ago protein to the target nucleic acid sequence. According to certain aspects, the spacer sequence is between about 1 and about 5 nucleotides in length. Aspects of the present disclosure are directed to methods of making or providing such guide DNA sequences as described herein by expressing constructs encoding such guide DNA using promoters and terminators and optionally other genetic elements as described herein.

According to certain aspects, the guide DNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to one aspect, an exemplary guide DNA is a 5'-phosphorylated DNA sequence. According to one aspect, an exemplary guide DNA is a 20 bp DNA sequence. According to one aspect, an exemplary guide DNA is a 5'-phosphorylated 20 bp DNA sequence. According to one aspect, the spacer sequence need not hybridize 100% to the target nucleic acid sequence. According to one aspect, the spacer sequence may include between 1 to 5 mismatches with the target nucleic acid sequence.

According to one aspect, the guide DNA is exogenous to the cell. According to one aspect, the guide DNA is foreign to the cell. According to one aspect, the guide DNA is non-naturally occurring within the cell.

Donor Description

The term "donor nucleic acid" includes a nucleic acid sequence which is to be inserted into a target nucleic acid sequence which has been cut or nicked according to methods described herein. The donor nucleic acid sequence may be expressed by the cell.

According to one aspect, the donor nucleic acid is exogenous to the cell. According to one aspect, the donor nucleic acid is foreign to the cell. According to one aspect, the donor nucleic acid is non-naturally occurring within the cell.

Transcription Regulator Description

According to one aspect, an engineered Ago protein and guide DNA system is provided which enables DNA-guided nucleic acid regulation, such as genomic DNA regulation, in eukaryotic cells by tethering transcriptional regulatory proteins or domains to either a nuclease-null Ago protein or to a guide DNA. According to one aspect of the present disclosure, one or more transcriptional regulatory proteins or domains (such terms are used interchangeably) are joined or otherwise connected to a nuclease-deficient or nuclease null Ago protein or one or more guide DNA (gDNA). The transcriptional regulatory domains correspond to targeted loci. Accordingly, aspects of the present disclosure include methods and materials for localizing transcriptional regulatory domains to targeted loci by fusing, connecting or joining such domains to either a nuclease null Ago or to the gDNA.

According to one aspect, a nuclease null Ago-transcriptional regulator fusion capable of transcriptional regulation, either transcriptional activation or transcriptional repression, is provided. According to one aspect, a VP64 activation domain is joined, fused, connected or otherwise tethered to the C terminus of a nuclease null Ago protein. According to one method, the transcriptional regulatory domain is provided to the site of a target nucleic acid sequence by the nuclease null Ago protein and a guide DNA. According to one method, a nuclease null Ago protein attached, connected, bound or fused to a transcriptional regulatory domain is provided within a cell along with one or more guide DNA sequences. The nuclease null Ago protein with the transcriptional regulatory domain attached, connected, bound or fused thereto co-localize with a guide DNA at or near a target nucleic acid sequence. The transcriptional regulatory domain regulates expression of the target nucleic acid sequence. According to a specific aspect, a nuclease null Ago-VP64 construct activates transcription of a gene, such as a reporter construct, when combined with a gDNA(s) targeting a sequence(s) near the promoter, thereby displaying DNA-guided transcriptional activation. According to a specific aspect, a nuclease null Ago-repressor construct represses transcription of a gene, such as a reporter construct, when combined with a gDNA(s) targeting a sequence(s) near the promoter, thereby displaying DNA-guided transcriptional repression. According to a specific aspect, a nuclease null Ago represses transcription of a gene, such as a reporter construct, when combined with a gDNA(s) targeting a sequence(s) near the promoter, thereby displaying DNA-guided transcriptional repression by blocking transcription due to binding.

According to one aspect, a gDNA-transcriptional regulator fusion capable of transcriptional regulation, either transcriptional activation or transcriptional repression, is provided. According to one aspect, a VP64 activation domain is joined, fused, connected or otherwise tethered to a gDNA sequence. According to one method, the transcriptional regulatory domain is provided to the site of a target nucleic acid sequence by the guide DNA sequence. According to one method, a nuclease null Ago protein is provided within a cell along with a guide DNA sequence attached, connected, bound or fused to a transcriptional regulatory domain. The nuclease null Ago protein co-localizes with a guide DNA at or near a target nucleic acid sequence. The transcriptional regulatory domain regulates expression of the target nucleic acid sequence. According to a specific aspect, a gDNA-VP64 construct activates transcription of a gene, such as a reporter construct, when co-localized with a nuclease null Ago targeting a sequence(s) near the promoter, thereby displaying DNA-guided transcriptional activation. According to a specific aspect, a gDNA-repressor construct represses transcription of a gene, such as a reporter construct, when co-localized with a nuclease null Ago targeting a sequence(s) near the promoter, thereby displaying DNA-guided transcriptional repression.

Transcriptional regulator proteins or domains which are transcriptional activators include VP16 and VP64 and others readily identifiable by those skilled in the art based on the present disclosure.

According to one aspect, the transcriptional regulator or domain is a chromatin modifier, remodeller, or histone modifier including enzymes involved in histone acetylation, methylation, demethylation, phosphorylation, ubiquitination, sumoylation, ADP-ribosylation, deimination, and proline isomerization. Exemplary regulators include DNA methyltransferases, histone methyltransferases and demethylases, histone acetyltransferase and deacetylases, etc. are well known in the art. Non-limiting disclosures as found in the following references are hereby incorporated by reference in their entireties. Taiping Chen & Sharon Y. R. Dent, Chromatin modifiers and remodeller: regulators of cellular differentiation, *Nature Reviews Genetics*, Vol. 15, Pp: 93-106 (2014). Andrew J Bannister and Tony Kouzarides, Regulation of chromatin by histone modifications, Cell Research, Vol. 21, Pp 381-395, (2011).

According to one aspect, the transcriptional regulator protein or domain upregulates expression of the target nucleic acid sequence.

According to one aspect, the transcriptional regulator protein or domain upregulates expression of the target nucleic acid sequence to treat a disease or detrimental condition.

According to one aspect, the transcriptional regulator is exogenous to the cell. According to one aspect, the transcriptional regulator is foreign to the cell. According to one aspect, the transcriptional regulator is non-naturally occurring within the cell.

Target Nucleic Acid Sequence

A target nucleic acid sequence includes any nucleic acid sequence, such as a genomic nucleic acid sequence or a gene to which a co-localization complex as described herein can be useful to either cut, nick or regulate. Target nucleic acids include nucleic acid sequences capable of being expressed into proteins. According to one aspect, the target nucleic acid is genomic DNA, mitochondrial DNA, plastid DNA, viral DNA, exogenous DNA or cellular RNA.

For purposes of the present disclosure, DNA, such as genomic DNA, can include the target nucleic acid sequence and a co-localization complex can bind to or otherwise co-localize with the target nucleic acid sequence or adjacent or near the target nucleic acid sequence and in a manner in which the co-localization complex may have a desired effect on the target nucleic acid sequence. One of skill based on the present disclosure will readily be able to identify or design guide DNAs and Ago proteins which co-localize to a target nucleic acid sequence. According to one aspect, the target nucleic acid is an A-T rich nucleic acid sequence with an initiating 5'-phosphorylated nucleotide C.

Foreign Nucleic Acids Description

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. According to one aspect, a foreign nucleic acid is exogenous to the cell. According to one aspect, a foreign nucleic acid is non-naturally occurring within the cell.

Cells

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to cut, nick or regulate a target nucleic acid. Such cells may include those which are deficient in expression of a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment. Such cells may include those which over express a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional depressor resulting in down-regulation of the target nucleic acid and corresponding expression of the particular protein. In this manner, the methods described herein provide therapeutic treatment.

According to one aspect, the cell is a eukaryotic cell or a prokaryotic cell. According to one aspect, the cell is a yeast cell, bacterial cell, fungal cell, a plant cell or an animal cell. According to one aspect, the cell is a mammalian cell. According to one aspect, the cell is a human cell. According to one aspect, the cell is a stem cell whether adult or embryonic. According to one aspect, the cell is a pluripotent stem cell. According to one aspect, the cell is an induced pluripotent stem cell. According to one aspect, the cell is a human induced pluripotent stem cell. According to one aspect, the cell is in vitro, in vivo or ex vivo.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory Elements and Terminators and Tags

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

Delivery Description

Embodiments of the present disclosure are directed to a method of delivering an Ago protein to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, an Ago protein or a nucleic acid encoding the Ago protein.

Embodiments of the present disclosure are directed to a method of delivering a guide DNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a guide DNA or a nucleic acid encoding the guide DNA.

Embodiments of the present disclosure are directed to a method of delivering an Ago protein and a guide DNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, an Ago protein or a nucleic acid encoding the Ago protein and a guide DNA or a nucleic acid encoding the guide DNA.

Diseases and Conditions

Diseases and detrimental conditions may be characterized by abnormal loss of expression or underexpression of a particular protein or abnormal gain or overexpression of a particular protein. Such diseases or detrimental conditions can be treated by upregulation or down regulation of the particular protein. Accordingly, methods of treating a disease or detrimental condition are provided where the co-localization complex as described herein associates or otherwise binds to a target nucleic acid and the transcriptional activator of the co-localization complex upregulates expression of the target nucleic acid or the transcriptional repressor of the co-localization complex downregulates expression of the target nucleic acid. One of skill in the art will readily identify such diseases and detrimental conditions based on the present disclosure.

The following examples are set forth as being representative of the present disclosure. These examples are not to be construed as limiting the scope of the present disclosure as these and other equivalent embodiments will be apparent in view of the present disclosure, figures and accompanying claims.

Example I

Materials and Methods

Cell Lines

The 293 FT HEK cells were grown and maintained in Dulbecco's modified Eagle's medium (DMEM, Invitrogen) high glucose supplemented with 10% fetal bovine serum (Invitrogen), penicillin/streptomycin (pen/strep, Invitrogen) and nonessential amino acids (Invitrogen).

Primer Design

List of primers used herein are provided below.

| NCBI Gene Symbol | Sequence | SEQ ID NO: |
|---|---|---|
| TFAM | TGGGAAGGTCTGGAGCA | 1 |
|  | GCCAAGACAGATGAAAACCAC | 2 |
| NANOG | ATGTCTTCTGCTGAGATGCC | 3 |
|  | GAAGTGGGTTGTTTGCCTTTG | 4 |
| IL1B | CAGCCAATCTTCATTGCTCAAG | 5 |
|  | GAACAAGTCATCCTCATTGCC | 6 |
| TERT | CATGCCAAGCTCTCGCT | 7 |
|  | GATCTCCTCACGCAGACG | 8 |
| SOX2 | GCCTCACTTACAAGACAGCTC | 9 |
|  | GCCTCCAAGACCTAGCCTA | 10 |
| KLF4 | TTGACTTTGGGGTTCAGGTG | 11 |
|  | GCGAACGTGGAGAAAGATGG | 12 |

| NCBI Gene Symbol | Sequence | SEQ ID NO: |
|---|---|---|
| cMYC | TTCGGGTAGTGGAAAACCAG | 13 |
| | CAGTAGAAATACGGCTGCAC | 14 |
| RNA18s5 | GAGACTCTGGCATGCTAACTAG | 15 |
| | GGACATCTAAGGGCATCACAG | 16 |
| HBG1 | TGAATGTGGAAGATGCTGGA | 17 |
| | TTGCCATGTGCCTTGACTT | 18 |
| Oct4 | AATCCAGTCCCAGGACATCA | 19 |
| | CGTTTGGCTGAATACCTTCC | 20 |
| ASCL | GGAGCTTCTCGACTTCACCA | 21 |
| | AACGCCACTGACAAGAAAGC | 22 | siDNA (Guide DNA)

List of siDNAs used herein are provided below.

| TtAgo$_{NN}$-VP64 system | | | |
|---|---|---|---|
| Name of siDNA | Gene to activate | siDNA Sequence | SEQ ID NO: |
| TFAM-1 | TFAM | /5Phos/caaattattttagaaatcaa | 23 |
| TFAM-4 | TFAM | /5Phos/cagcggagcgtctcagttca | 24 |
| TFAM-5 | TFAM | /5Phos/cagccctggcttgaactgag | 25 |
| TFAM-7 | TFAM | /5Phos/cagaaatagtaacgggagag | 26 |
| TFAM-8 | TFAM | /5Phos/cacggaattaagctctgcgg | 27 |
| Ago-GC-15-1 | TFAM | /5Phos/catgttttataaagtaatta | 28 |
| Ago-GC-15-2 | TFAM | /5Phos/tattaaacttttgttgttt | 29 |
| Ago3-top | TFAM | /5Phos/caaaaagtttaatatccaaa | 30 |
| Ago-GC-20-1 | TFAM | /5Phos/catggtatataattactttta | 31 |
| Ago-3-top2 | TFAM | /5Phos/catttgaagaacaaaaaca | 32 |
| Ago2-bot | TFAM | /5Phos/catttgtataaatcttgctg | 33 |
| Target 3 TtAgo | TFAM | /5Phos/caacttaaatgtaacttctg | 34 |
| Ago-GC-13 | TFAM | /5Phos/catgttttataaagtaattatat | 35 |
| Ago-GC-19 | TFAM | /5Phos/caaaaagtttaatatccaaaa | 36 |
| Ago-GC-14 | TFAM | /5Phos/caaattattttagaaatcaacttaaat | 37 |
| ASLC1_1 | ASLC1 | /5Phos/caattcctagagccatttgtc | 38 |
| ASLC1_2 | ASLC2 | /5Phos/cattttttctgcccaaacccctt | 39 |
| ASLC1_3 | ASLC3 | /5Phos/caagttcttagtagaatccaa | 40 |
| ASLC1_4 | ASLC4 | /5Phos/cacttttttttcactgttctgg | 41 |
| Nanog_1 | NANOG | /5Phos/cagctacttttgcattacaat | 42 |
| Nanog_2 | NANOG | /5Phos/caggttctgttgctcggtttt | 43 |
| Nanog_3 | NANOG | /5Phos/cattcctgttgaaccatattc | 44 |
| Nanog_4 | NANOG | /5Phos/ctaatttttgtatttttagta | 45 |
| HBG1_1 | HBG1 | /5Phos/caatagtcttagagtatcca | 46 |
| HBG1_2 | HBG2 | /5Phos/caaaggctataaaaaaaatta | 47 |
| HBG1_3 | HBG3 | /5Phos/cagttttctctaatttattc | 48 |
| HBG1_4 | HBG4 | /5Phos/caagaaggtaaaaacggct | 49 |
| IL1B_1 | IL1B | /5Phos/cataaaaacagcgagggagaa | 50 |
| IL1B_2 | IL1B | /5Phos/caggtattcaacagagaaatt | 51 |

| Name | Gene | Sequence | SEQ ID NO: |
|---|---|---|---|
| IL1B_3 | IL1B | /5Phos/caatactcttttcccctttcc | 52 |
| IL1B_4 | IL1B | /5Phos/caggaaaacaatgcatatttg | 53 |
| TERT_1 | TERT | /5Phos/catagaaaacacaattttaaaa | 54 |
| TERT_2 | TERT | /5Phos/cagtttctgaaagtaggaaa | 55 |
| TERT_3 | TERT | /5Phos/catttcccacccttttctcga | 56 |
| TERT_4 | TERT | /5Phos/catttctctttgcaggttct | 57 |
| GDF11-1 | GDF11 | /5phos/ attttgtctccactctaac | 58 |
| GDF11-2 | GDF11 | /5phos/ ttcctccttcttggttctgt | 59 |
| GDF11-3 | GDF11 | /5phos/ tcttcttttcctccttgtc | 60 |

Cas9$_{NN}$-VP64 system

| Name of gRNA | Gene | gRNA targeting sequence | PAM | SEQ ID NO: |
|---|---|---|---|---|
| gRNA 2 | TFAM | ctcggagttcagaaatagta | acggga | 61 |
| gRNA3 | TFAM | ttaagctctgcggtaaggcc | ttggaa | 62 |
| SP1 | TFAM | acctaaaaatgcagattcca | agg | 63 |
| SP2 | TFAM | cgcctctcccgttactattt | ggg | 64 |
| SP3 | TFAM | acacacggaattaagctctg | egg | 65 |
| SP4 | TFAM | tcgctaaaatgaagattaat | ggg | 66 |
| SP5 | TFAM | ttagaacttgttaaattctg | ggg | 67 |

TtAgo$_{NN}$ repressor system

| Name of siDNA | SEQ ID NO: | siDNA Sequence |
|---|---|---|
| TFAM-1 | 68 | /5Phos/ctacagaactaattagaaga |
| TFAM-2 | 69 | /5Phos/cttcctgattcaaagaaaaa |
| TFAM-3 | 70 | /5Phos/cttctttatatacctgccac |
| Sox2-1 | 71 | /5Phos/caacatgatggagacggagc |
| Sox2-2 | 72 | /5Phos/catgatgcaggaccagctgg |
| Sox2-3 | 73 | /5Phos/cttcacatgtcccagcacta |
| Oct4.1 | 74 | /5Phos/ctctttctgtccttcacga |
| Oct4.2 | 75 | /5Phos/ctacagactattccttgggg |
| Oct4.3 | 76 | /5Phos/cttacaagtcttctgcctttt |
| KLf-2.1 | 77 | /5Phos/cttctccactttcgccagcc |
| KLf-2.2 | 78 | /5Phos/cttctgctggcgccgcccg |
| KLf-2.3 | 79 | /5Phos/cttcggtctcttcgacgacg |
| cmyc.1 | 80 | /5Phos/ctggattttttcgggtagt |
| cmyc.2 | 81 | /5Phos/ctcaacgttagcttcaccaa |
| cmyc.3 | 82 | /5Phos/cagccgtatttctactgcga |
| NANOG.1 | 83 | /5Phos/cttgctttgaagcatccgac |
| NANOG.2 | 84 | /5Phos/cttcacctatgcctgtgatt |
| NANOG.3 | 85 | /5Phos/caaatgtcttctgctgagat |
| HBG1.1 | 86 | /5Phos/catttcacagaggaggacaa |
| HBG1.2 | 87 | /5Phos/ctggaggagaaaccctggga |
| HBG1.3 | 88 | /5Phos/cttttgacagctttggcaacc |
| IL1B.1 | 89 | /5Phos/ctcgccagtgaaatgatggc |
| IL1B.2 | 90 | /5Phos/caatgaggatgacttgttct |
| IL1B.3 | 91 | /5Phos/ctttgaagctgatggcccta |
| TERT.1 | 92 | /5Phos/ctccccgctgccgagccgtg |
| TERT.2 | 93 | /5Phos/ctgcgcagccactaccgcga |
| TERT.3 | 94 | /5Phos/cttccgcgcgctggtggcc |

Plasmids

The ttAGo-VP64 and ttAgo fragments (Genewiz) were synthesized and cloned into pCdna3.1 topo ct-gfp (Invitrogen) plasmids according to the manufacture's' instruction. The sequence information of the vector is provided below.

ttAgo-VP64 sequence (NLS-VP64 is highlighted in bold and italics)

(SEQ ID NO: 95)
ATGAACCACCTGGGTAAAACTGAAGTATTCCTGAACCGTTTCGCACTGagaccacttaat
CCGGAAGAACTGCGTCCGTGGCGTCTGGAAGTTGTTCTGGACCCGCCGCCGGGTC
GTGAAGAAGTTTACCCGCTGCTGGCTCAGGTTGCTCGTCGTGCTGGTGGTGTTAC
CGTTCGTATGGGTGACGGTCTGGCTTCTTGGTCTCCGCCGGAAgtattagtacttGAAGG
TACCCTGGCTCGTATGGGTCAGACCTACgcatatcgtttatatccaAAAGGTCGTCGTCCGCT
GgatccgaaggatcctGGTGAACGTTCTGTTCTGTCTgcattagctagaCGTCTGCTGCAGGAAC
GTCTGCGTCGTCTGGAAGGTGTTTGGGTTGAAGGTCTGGCTGTTTACCGTCGTGA
ACACGCTCGTGGTCCGGGTTGGCGTGTTCTGGGTGGTGCTGTTCTGGACCTGTGG
GTTTCTGACTCTGGTGCTTTCCTGCTGGAAGTTGACCCGGCTTACCGTATCCTGTG
CGAAATGTCTCTGGAAGCTTGGCTGGCTCAGGGTCACCCGCTGCCGAAACGTGTT
CGTAACGCTTACGACCGTCGTACCTGGGAActgctaagattaGGTGAAGAAGACCCGAA
AGAACTGCCGCTGCCGGGTGGTCTGTCTCTGCTGGACTACCACGCTTCTAAAGGT
CGTCTGCAGGGTCGTGAAggcgggagagtaGCTTGGGTTGCTGACCCGAAAGACCCGC
GTAAACCGATCCCGCACCTGACCGGTCTGCTGGTTCCGGTTCTGACCCTGGAAGA
CCTGCACGAGGAAGAAGGTTCTCTGGCTCTGTCTCTGCCGTGGGAAGAACGTCGT
CGTCGTACCCGTGAAATCGCTTCTTGGATCGGTCGTCGTCTGGGTCTGGGTACCC
CGGAAGCTGTTCGTGCTCAGGCTTACCGTCTGTCTATCCCGAAACTGATGGGTCG
TCGTGCTGTTTCTAAACCGGCTGACGCTCTGCGTGTTGGTTTCTACCGTGCTCAGG
AAACCgcgttagccctttttacgaCTGGACGGTGCTCAGGGTTGGCCGGAATTCCTGCGTCGG
GCTCTGCTGCGTGCTTTCGGTGCTTCTGGTGCTTCTCTGCGTCTGCACACCCTGCA
CGCTCACCCGTCTCAGGGTCTGGCTTTCCGTGAAGCTCTGCGTAAAGCTAAAGAA
GAAGGTGTTCAGGCTGTTCTGGTTCTGACCCCGCCGATGGCTTGGGAAGACCGTA
ACCGTCTGAAAGCTcttttactgagagagggcctgccgagcCAGATCCTGAACGTTCCGCTGCGT
GAAGAAGAACGTCACCGTTGGGAAAACGCTCTGCTGGGTCTGCTGGCTAAAGCT
GGTCTGCAGGTTGTTGCTCTGTCTGGTGCTTACCCGGCTGAACTGGCTGTTGGTTT
CGcCGCTGGTGGTCGTGAATCTTTCCGTTTCGGTGGTGCTGCTTGCGCTGTTGGTG
GTGACGGTGGTCACCTGCTGTGGACCCTGCCGGAAGCTCAGGCTGGTGAACGTA
TCCCGCAGGAAGTTGTTTGGGACCTGCTGGAAGAAACCCTGTGGGCTTTCCGTCG
TAAAGCTGGTCGTCTGCCGTCTCGTGTTCTGCTGCTGCGTGcCGGTCGTGTTCCGC
AGGACGAATTCGCTCTGGCTttagaagcgttagcgCGTGAAGGTATCGCTTACGACCTGGT
TTCTGTTCGTAAATCTGGTGGTGGTCGTGTTTACCCGGTTCAGGGTCGTCTGGCTG
ACGGTCTGTACGTTCCGCTGGAAGACAAAACCTTCCTGCTGCTGACCGTTCACCG
TGACTTCCGTGGTACCCCGCGTCCGCTGAAACTGGTTCACGAAGCTGGTGACACC
CCGCTGGAAGCTCTGGCTCACCAGATCTTCCACCTGACCCGTCTGTACCCGGCTT
CTGGTTTCGCTTTCCCGCGTCTGCCGGCTCCGCTGCACCTGGCTGACCGTCTGGTT
AAAGAAGTTGGTCGTCTGGGTATCCGTCACCTGAAAGAAGTTGACCGTGAAAAA
CTGTTCTTCGTT*CCCAAGAAGAAGAGAAAGGTGGAGGCCAGCGGTTCCGGACGGG*

-continued

```
CTGACGCATTGGACGATTTTGATCTGGATATGCTGGGAAGTGACGCCCTCGATGAT

TTTGACCTTGACATGCTTGGTTCGGATGCCCTTGATGACTTTGACCTCGACATGCT

CGGCAGTGACGCCCTTGATGATTTCGACCTGGACATGCTGATTAAC
```

Transfection and QPCR Analysis

293 T reporter cells were seeded at densities of $5*10^4$ cells per well in 96-well plate and transfected them with 300 ng of each ttAgo-VP64 plasmid and 300 ng siDNA using Lipofectamine 2000 following the manufacturer's protocols. The cells were harvested 36 hours after transfection and RT-QPCR was performed using cDNA to CT II kit (Invitrogen). All the RT-QPCR data is normalized with 18sRNA control and the sequence of the primers are provided herein.

Western Blot
Cell Harvest 7 million 293 T reporter cells were seeded in each T175 plate and were transfected with 12 µg of TtAgo-VP64 plasmid and 12 µg siDNA using 60 µL of Lipofectamine 2000 following the manufacturer's protocols. The cells were harvested 1 week after transfection by removing culture medium from the adherent cells, rinsing the cells in PBS, and adding M-PER (Pierce) reagent according to protocol. The lysate was collected and transferred into a microcentifuge tube. The samples were spun at 14,000×g for 10 minutes at 4° C. to pellet the cell debris. The supernatant was then transferred to another tube for analysis and frozen at −20° C. overnight.

Western Blot

Supernatant was thawed on ice. The Pierce™ BCA Protein Assay Kit was used to quantify protein content (1:12.5 dilution) in each sample according to the manufacturer's protocol. The samples were then normalized to lowest concentration. Next, Laemmli Buffer was added at 1:6 dilution and boiled at 95° C. for 5 minutes. Gels were then loaded with 30 µL of sample at 60 V to stack for 20 minutes and then 100 V for 1 hour. PVDF was pre-treated with 20% methanol and then transfer buffer (25 mM Tris, 192 mM glycine, 10% methanol). The wet transfer sandwich was then prepared according to manufacturer's protocol and transferred for 1 hour at 100 V. Membranes were then trimmed and incubated in 5% milk TBST (Tris-buffered saline, 0.1% Tween-20). The membrane was then incubated in either TFAM antibody (Aviva Systems Biology #0AAF02353 or Tubulin (TUBB3) antibody (Aviva Systems #OAAD00318) in 5% milk overnight at 4° C. The membranes were then washed 3 times in 1×TBST for 5 minutes each. Next, the membranes were incubated in anti-Rabbit in 5% milk for 1 hour and washed 3 times for 5 minutes in 1×TB ST. The membranes were then exposed to the Bio-Rad Clarity™ ECL substrate according to manufacturer's instructions and imaged using x-ray film. Densitometry of each band was quantified using ImageJ toolkit.

Gel Shifting Assay
Protein Purification

Plasmid pWUR-702 and pWUR-703 containing strept-tagged TtAgo proteins from Addgene are transformed into Rosetta™ 2(DE3) strain (Agilent) and grown in 5 mL of 2YT media with 100 µg/mL of Spectinomycin overnight. 250 mL media are inoculated with the overnight cultures and protein expression is induced with 1 mM of IPTG at OD600 around 0.6-0.8. The cells are incubated at shaker at 20° C. for 16 h and harvest by centrifuge. Cell pellet is then resuspended in Buffer A (20 mM Tris-HCl pH 7.6, 1 M NaCl and 2 mM $MgCl_2$) and lysed with french pressure cell. The protein is purified over 3 mL Strep-Tactin® Superflow® resin with protocol suggested by vendor. Protein are eluted into Buffer A plus 2.5 mM d-Desthiobiotin and stored in −80° C. upon adding one volume of 80% glycerol.

Gel Shift Assay

5'-Biotinylated or unlabeled competing substrate ssDNA, dsDNA and 5'-phosphorylated guide DNA are purchased from Integrated DNA Technology without further purification. Binding reactions contain the following components: 1 µM of 5'-biontin-substrate, 1 µM of guide DNA, 0.5 mg/mL of Salmon sperm DNA (Invitrogen), 5 µM of TtAgo protein, 100 µM of competing substrate (optional), 20 mM HEPES-KOH pH 7.6, 100 mM KCl, 5 mM $MgCl_2$, 1 mM DTT. The reactions are incubated at 37° C. for 1 h and resolved on 6% DNA retardation gel (Invitrogen) with running buffer containing 1×TBE and 5 mM $MgCl_2$. The DNA are transferred to nitrocellulose membrane by iBlot (Invitrogen) dry transfer, cross-linked under UV and stained by the LightShift Chemiluminescent EMSA Kit (Thermo Scientific) according to vendor's manual instruction.

Example II

Engineered Ago and Guide DNA

A DNA-guided Ago system is provided for genome engineering. A TtAgo protein and siDNA components are engineered to both activate and repress gene expression in human cells. As indicated in FIG. 1, it was confirmed that TtAgo/siDNA has sequence specific single stranded DNA (ssDNA) binding activity in vitro at 37° C. Purified ttAgo protein was incubated with either a dsDNA (double stranded DNA) or ssDNA (single stranded DNA) substrate wt/wo siDNA at 37° C. and the binding of ttAgo with the substrate was examined by gel shifting assay. Binding of ttAgo with ssDNA with the presence of siDNA (lane 9 from the left) was detected. The sequence of substrate and siDNA are identified in FIG. 1.

TtAgo/siDNA systems were engineered for gene suppression and activation in human cells. The gene suppression system features a CMV promoter driving a human optimized codon Ago double site mutant $TtAgo_{NN}$(D478A, D546A), which removes its nuclease activity, fused to a C-terminal SV40 nuclear localization signal (NLS). The activation system features an activation domain, VP64, on the C-terminus (FIG. 2A). Guide siDNA were selected in AT rich sequences within the promoter (for activation) or exon 1/2 (for suppression) region with a 5' dC initiating nucleotide. See D. C. Swarts, M. M. Jore, E. R. Westra, Y. Zhu, J. H. Janssen, A. P. Snijders, Y. Wang, D. J. Patel, J. Berenguer, S. J. Brouns, J. van der Oost, DNA-guided DNA interference by a prokaryotic Argonaute. Nature 507, 258-261 (2014) hereby incorporated by reference in its entirety.

To test if $TtAgo_{NN}$-VP64/siDNA activates human endogenous genes, two siDNAs (siDNA TFAM-7 and siDNA TFAM-8) were designed to target the promoter regions of transcription factor A mitochondria (TFAM). See FIG. 2B and sequences provided below.

| Name | Gene | siDNA sequence for TtAgo system | SEQ ID NO: |
|---|---|---|---|
| TFAM-7 | TFAM | /5Phos/cagaaatagtaacgggagag | 26 |
| TFAM-8 | TFAM | /5Phos/cacggaattaagctctgcgg | 27 |

| Name | Gene | gRNA targeting sequence for CRISPR/Cas-ST | PAM |
|---|---|---|---|
| gRNA 2 | TFAM | ctcggagttcagaaatagta | acggga 61 |
| gRNA 3 | TFAM | ttaagctctgcggtaaggcc | ttggaa 62 |

As a comparison, we designed two *Streptococcus thermophiles* Cas9-VP64 (Cas9ST-VP64)/gRNA constructs were designed according to K. M. Esvelt, P. Mali, J. L. Braff, M. Moosburner, S. J. Yaung, G. M. Church, Orthogonal Cas9 proteins for RNA-guided gene regulation and editing. *Nat Methods* 10, 1116-1121 (2013) hereby incorporated by reference in its entirety (gRNA 2 and gRNA 3) targeting the same regions. See FIG. 2C. Delivery of TtAgo$_{NN}$-VP64/siDNA into HEK 293 cells demonstrated robust TFAM activation of 20-fold and 60-fold increase in gene expression respectively, comparable to the level achieved by Cas9-VP64/gRNA targeting the same regions (see FIG. 2C). TtAgo$_{NN}$-VP64 provided higher activation than the Cas9ST-VP64 system.

According to one aspect, lower melting temperature (Tm) AT-rich regions of target nucleic acids are targeted by the Ago systems described herein using TtAgo$_{NN}$, which does not have a helicase domain, and therefore increases the likelihood for activation. 14 siDNAs targeting the TFAM promoter as a function of Tm were designed as indicated herein. A reverse correlation of Tm of the targeting sites and TtAgo$_{NN}$-VP64/siDNA activation activities were observed as indicated in FIG. 2D). Because TtAgo lacks a helicase domain, co-transfection of the *S. pyogenes* Cas9 null mutant (Cas9$_{SP-NN}$) (see P. Mali, L. Yang, K. M. Esvelt, J. Aach, M. Guell, J. E. DiCarlo, J. E. Norville, G. M. Church, RNA-guided human genome engineering via Cas9. *Science* 339, 823-826 (2013) hereby incorporated by reference in its entirety) improves activation efficiency of the TtAgo$_{NN}$-VP64 system by unwinding the dsDNA substrate. To this end, a siDNA with low activation performance (TFAM-4, Activation ~1±0.2 compared to TtAgo$_{NN}$-VP64 alone) was selected and co-transfected with Cas9SP$_{NN}$/gRNA systems as described in *Science* 339, 823-826 (2013) targeting between 46 and 187 bp away from the siDNA target site. Binding of Cas9SP$_{NN}$/gRNA nearby improves activation of TtAgo$_{NN}$-VP64/siDNA, and the optimal efficiency was seen when the two systems are ~128 bp apart. See FIGS. 3A and 3B. This optimal distance most likely reduces the effects of steric hindrance between the two systems and allows for TtAgo$_{NN}$-VP64 to access its ssDNA target which otherwise is in the dsDNA form. TtAgo$_{NN}$-VP64 activates genes in the human genome, preferably at A-T rich regions, when the ssDNA substrate (target nucleic acid sequence) is more accessible.

Figures 3A, 3B:
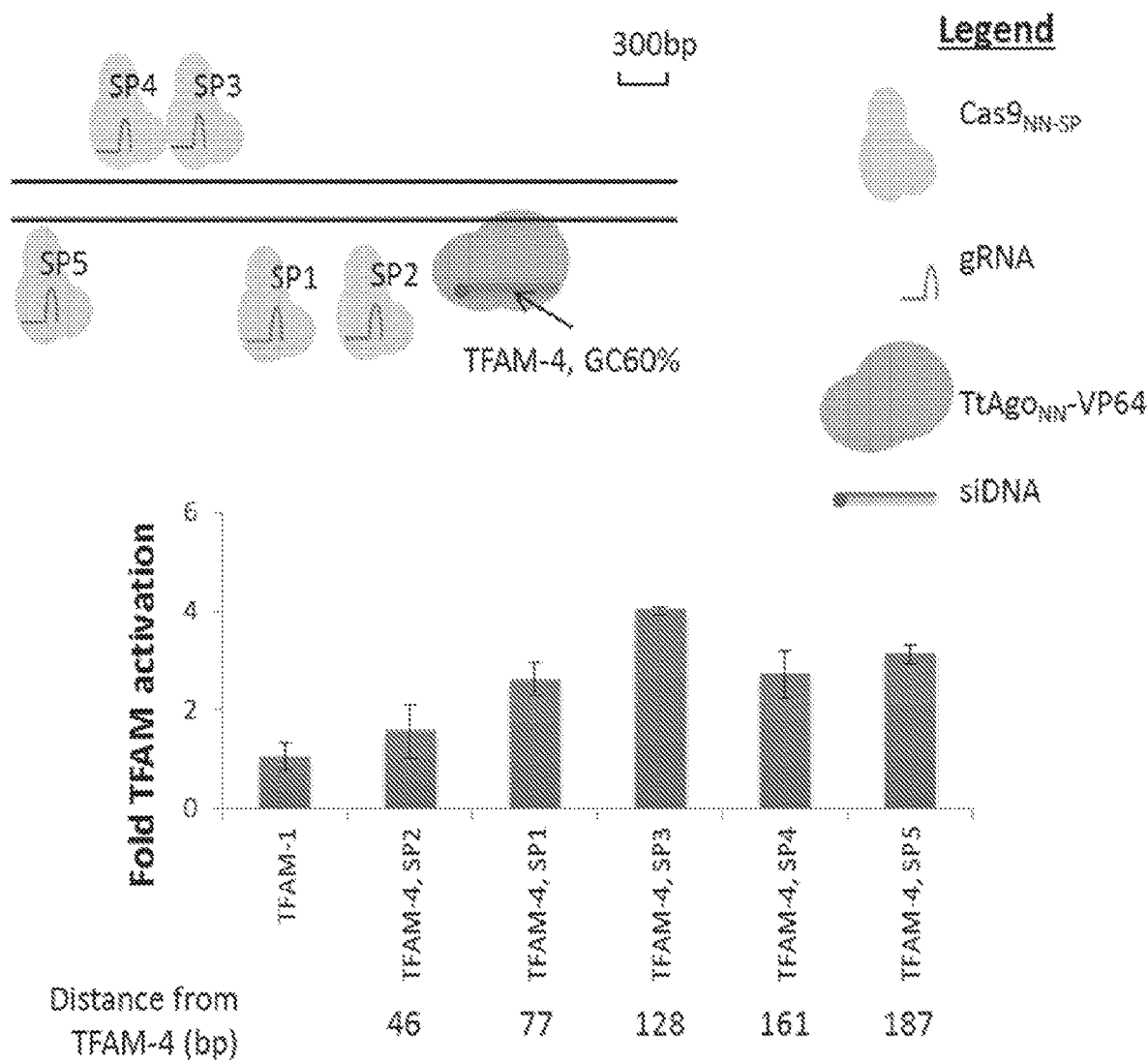
FIG. 3A depicts a schematic of guide RNA designed to localize nuclease null Cas9 at various distances from TtAgo-VP64/siDNA_TFAM-4.
FIG. 3B depicts data of Fold TFAM Activation.

As shown in FIGS. 3A and 3B, the DNA helicase domain of the null mutant Cas9$_{NN-SP}$/gRNA systems improves activation of TtAgo$_{NN}$-VP64/siDNA from 1- to 4-fold when the Cas9 system binds 77 bp-161 bp upstream of TtAgo binding on the TFAM promoter. FIG. 3A is a schematic of a design of 5 gRNAs to localize Cas9NN-sp at varying distances from TtAgo-VP64/siDNA_TFAM-4. Each gRNA is named 'SPX', where SP denotes the species of Cas9 protein, and X is 1, 2, 3, 4, or 5 to identify the gRNA used. The legend highlights that the gRNA and Cas9$_{NN-SP}$ combine as a unit to localize the system to a specific area in the genome. Similarly, the TtAgo-VP64 and siDNA (TFAM-4) combine as a unit to localize the system to a specific area in the genome. The specific gRNA targeting sequences are described herein. FIG. 3B is data directed to TtAgo$_{NN}$-VP64/siDNA_TFAM-4 activation activities when combining with Cas9$_{NN-SP}$/gRNA as measured by RT-PCR to amplify a 150 bp region of exon 1 of TFAM. Cas9$_{NN-SP}$/gRNAs with distance 46 bp-187 bp to siDNA_TFAM-4 binding site increases the TtAgo$_{NN}$-VP64/siDNA_TFAM-4 activities 4 fold.

Figure 4:
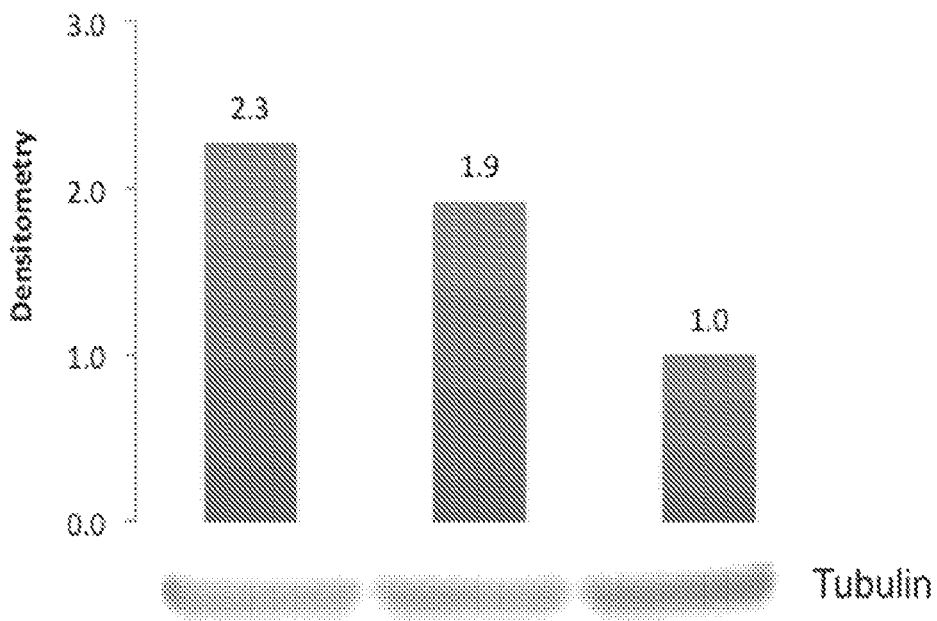
FIG. 4 depicts immunoblots and data of DNA-guided activation TFAM (25 kDa).

The methods described herein increased mRNA levels using TtAgo$_{NN}$-VP64/siDNA. Methods described herein using TtAgo$_{NN}$-VP64/siDNA also increased protein levels. FIG. 4 depicts immunoblots showing DNA-guided activation of TFAM (25 kDa). Tubulin (50 kDA) served as a control. Intensity of each blot band, I, was calculated using ImageJ software. Densitometry of TFAM protein was quantified using the equation above. Activators for TFAM (TFAM-1 and TFAM-3 siDNA, respectively) were selected to quantify the amount of TFAM protein in each population after 3 days of transfection. As shown in FIG. 4, a 2.3-fold and 1.9-fold increase of TFAM protein, respectively, was confirmed using the TtAgo$_{NN}$-VP64/TFAM-1 siDNA.

Figure 5:
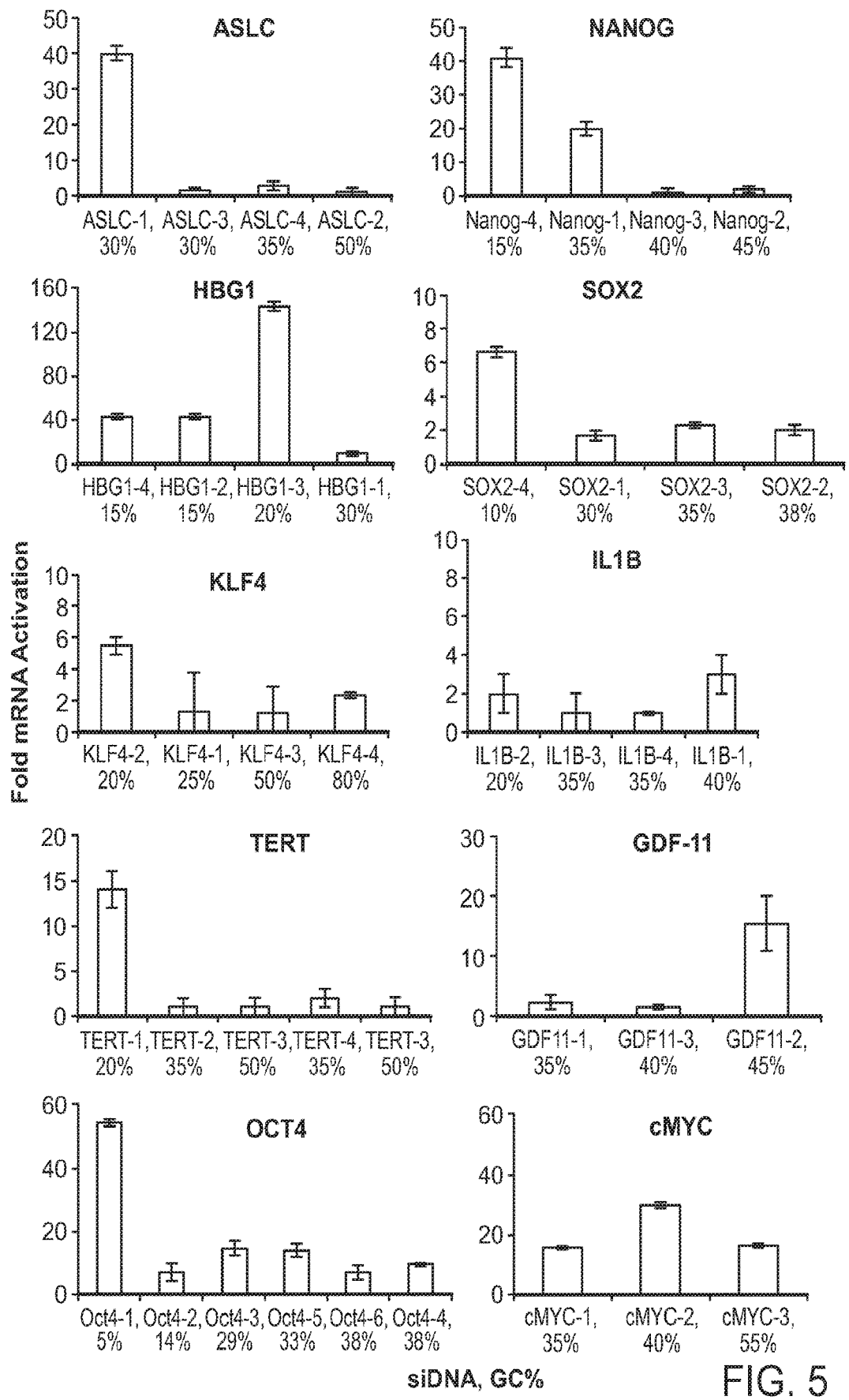
FIG. 5 is directed to data demonstrating that DNA-guided TtAgo$_{NN}$-VP64 activates a panel of genes. 3-6 siDNA targeting sequences were designed for the promoter region of 9 genes. The melting temperature (Tm), which is expressed as GC %, of each siDNA affects the efficiency of endogenous activation. All levels of activation were measured by RT-QPCR and normalized to experiments transfected by TtAgo$_{NN}$-VP64 alone. The 18 s housekeeping gene was used as a control. Plotted values represent the average. Error bars represent the standard deviation from the mean (N=3).

To test the effectiveness of TtAgo$_{NN}$-VP64 activation system across the genome, a panel of endogenous genes (GDF11, ASLC, NANOG, HBG1, IL1B, TERT, SOX2, KLF4, cMYC, and OCT4) was selected and between 3-6 siDNAs were designed targeting AT-rich areas of the respective promoter region (See FIG. 5). Among the ten genes tested, nine genes were successfully activated by a single TtAgo$_{NN}$-VP64/siDNA complex and the activation level showed predicable fashion based on AT content (See FIG. 5). Notably, genes such as TERT and NANOG, that were previously not able to be activated by a single gRNA in the CRISPR/Cas9 system (see A. W. Cheng, H. Wang, H. Yang, L. Shi, Y. Katz, T. W. Theunissen, S. Rangarajan, C. S. Shivalila, D. B. Dadon, R. Jaenisch, Multiplexed activation of endogenous genes by CRISPR-on, an RNA-guided transcriptional activator system. *Cell research* 23, 1163-1171 (2013); P. Perez-Pinera, D. D. Kocak, C. M. Vockley, A. F. Adler, A. M. Kabadi, L. R. Polstein, P. I. Thakore, K. A. Glass, D. G. Ousterout, K. W. Leong, F. Guilak, G. E. Crawford, T. E. Reddy, C. A. Gersbach, RNA-guided gene activation by CRISPR-Cas9-based transcription factors. *Nat Methods* 10, 973-976 (2013)) have been robustly activated by a single siDNA in the TtAgo$_{NN}$-VP64/siDNA system. Moreover, TtAgo$_{NN}$-VP64/siDNA activated ASLC, HBG1, SOX2, and OCT4 better than Cas9/gRNA systems. Of note, HBG1-3 siDNA (20% GC, 143 fold activation) significantly outperformed HBG1-2 and HBG1-4 (each 15% GC, 43 and 43 fold activation).

Figure 6:
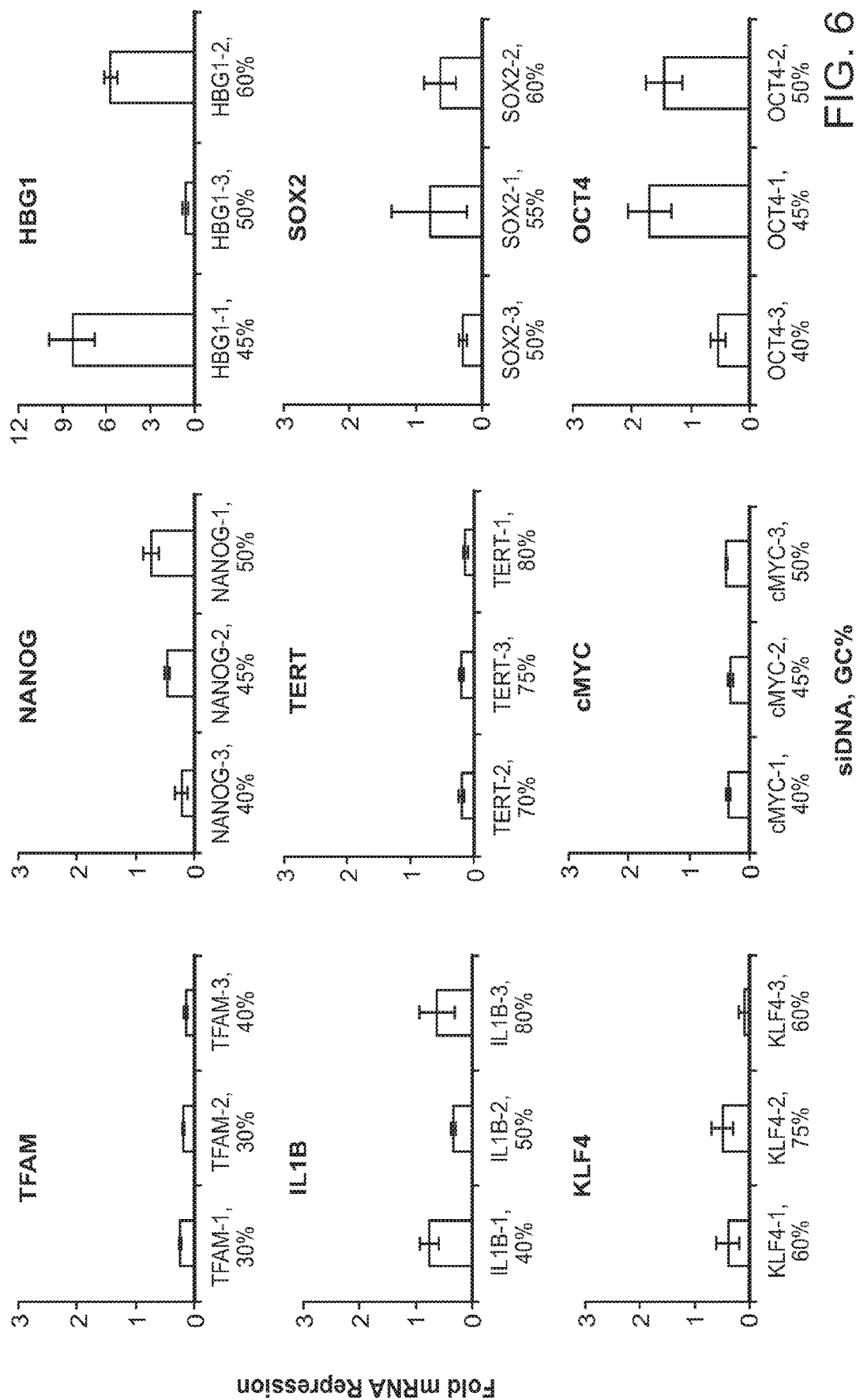
FIG. 6 is directed to data demonstrating that DNA-guided TtAgo$_{NN}$ represses a panel of genes. 3 siDNA targeting sequences were designed for exon 1 or 2 of 9 genes. GC % of each siDNA is listed. All levels of suppression were normalized to experiments transfected by TtAgo$_{NN}$ alone. The 18 s housekeeping gene was used as a control. Plotted values represent the average. Error bars represent the standard deviation from the mean (N=3).

The methods described herein utilize an Ago system to suppress gene expression. Gene suppression activity was demonstrated by interfering with or otherwise blocking the translational machinery. Three siDNA targeting exon 1 and/or 2 of each gene in the panel described previously (TFAM, NANOG, HBG1, IL1B, TERT, SOX2, KLF4, cMYC, and OCT4) were designed and HEK293 cells were transfected with TtAgo$_{NN}$ with siDNA respectively. Notably, 6 out of the 9 constructs tested demonstrated robust gene repression by 10-90% (see FIG. 6). TtAgo$_{NN}$/siDNAs targeting the exon 1 of HBG1 and OCT4 activated gene expression, while TtAgo$_{NN}$/siDNAs targeting exon 2 of HBG1 and OCT4 sufficiently repressed gene expression, likely resulting from interaction of TtAgo$_{NN}$ with transcription initiation complex.

Figure 7:
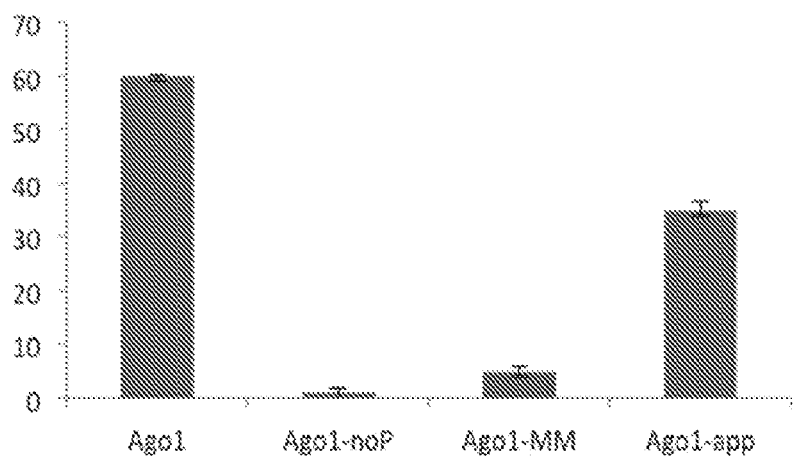
FIG. 7 depicts data 5 depicts data for TtAgo$_{NN}$-VP64/siDNA sequence specificity as measured by TFAM activation activities by TtAgo$_{NN}$-VP64/siDNA coupled with different siDNAs (SEQ ID NOS 99, 23, 100, and 101, respectively, in order of appearance).

FIG. 7 is directed to guide DNA sequence specificity. TtAgo$_{NN}$-VP64/siDNA sequence specificity as measured by TFAM activation activities by TtAgo$_{NN}$-VP64/siDNA coupled with different siDNAs was determined. As indicated in FIG. 7, a 5' phosphate on the guide DNA provided TtAgo$_{NN}$-VP64 activities. Mismatches may be allowed under certain circumstances. A mismatch in the middle of the siDNA recognition or spacer sequence showed reduced TtAgo$_{NN}$-VP64/siDNA activity.

What is claimed is:

1. A method of altering a eukaryotic cell comprising providing to the eukaryotic cell a guide DNA sequence complementary to a complementary target nucleic acid sequence, providing to the eukaryotic cell an argonaute (Ago) enzyme that interacts with the guide DNA sequence and cleaves the complementary target nucleic acid sequence in a site specific manner, and providing to the eukaryotic cell a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence, wherein the guide DNA sequence binds to the complementary target nucleic acid sequence and the Ago enzyme cleaves the complementary target nucleic acid sequence in a site specific manner that is facilitated by the unwinding of the guide RNA targeting target nucleic acid sequence.

2. The method of claim 1 wherein the guide RNA targeting target nucleic acid sequence and the complementary target nucleic acid sequence are about 75 to 150 base pairs apart.

3. The method of claim 1 further including the step of providing a donor sequence and wherein the donor sequence is inserted into the complementary target nucleic acid sequence.

4. The method of claim 1 wherein the eukaryotic cell is a yeast cell, a plant cell or a mammalian cell.

5. The method or claim 1 wherein the eukaryotic cell is a human cell.

6. The method of claim 1 wherein a plurality of guide DNAs are provided into the cell that are complementary to different complementary target nucleic acid sequences and the Ago enzyme cleaves the different complementary target nucleic acid sequences in a site specific manner.

7. A method of altering a eukaryotic cell comprising
providing to the eukaryotic cell a first nucleic acid sequence that is complementary to a complementary target nucleic acid sequence,
providing to the eukaryotic cell a second nucleic acid sequence encoding an argonaute (Ago) enzyme that interacts with the first nucleic acid sequence and cleaves the complementary target nucleic acid sequence in a site specific manner, and
providing to the eukaryotic cell a nuclease null Cas9 protein and a guide RNA, wherein the guide RNA is complementary to a guide RNA targeting target nucleic acid sequence,
wherein the nuclease null Cas9 and the guide RNA colocalize at the guide RNA targeting target nucleic acid sequence and unwind the guide RNA targeting target nucleic acid sequence,
wherein the first nucleic acid sequence is a guide DNA, wherein the second nucleic acid sequence is expressed, and
wherein the guide DNA sequence binds to the complementary target nucleic acid sequence and the Ago enzyme that is expressed from the second nucleic acid sequence cleaves the complementary target nucleic acid sequence in a site specific manner that is facilitated by the unwinding of the guide RNA targeting target nucleic acid sequence.

8. The method of claim 7 further including the step of providing a donor sequence and wherein the donor sequence is inserted into the complementary target nucleic acid sequence.

9. The method of claim 7 wherein the eukaryotic cell is a yeast cell, a plant cell or a mammalian cell.

10. The method or claim 7 wherein the eukaryotic cell is a human cell.

11. The method of claim 7 wherein a plurality of guide DNAs are provided into the cell that are complementary to different complementary target nucleic acid sequences and the Ago enzyme cleaves the different complementary target nucleic acid sequences in a site specific manner.

12. The method of claim 7 wherein the second nucleic acid sequence is present on a recombinant expression vector.

13. The method of claim 7 wherein the guide RNA targeting target nucleic acid sequence and the complementary target nucleic acid sequence are about 75 to 150 base pairs apart.

14. An in vitro eukaryotic cell comprising
a first nucleic acid sequence that is complementary to a complementary target nucleic acid sequence,
a second nucleic acid sequence encoding an argonaute (Ago) enzyme that interacts with the first nucleic acid sequence and cleaves the complementary target nucleic acid sequence in a site specific manner,
a nuclease null Cas9 protein and a guide RNA, wherein the guide RNA is complementary to a guide RNA targeting target nucleic acid sequence, wherein the nuclease null Cas9 and the guide RNA colocalize at the guide RNA targeting target nucleic acid sequence and unwind the guide RNA targeting target nucleic acid sequence,
wherein the first nucleic acid sequence is a guide DNA, and wherein the cell expresses the Ago enzyme, and wherein the guide DNA binds to the complementary target nucleic acid and the Ago enzyme cleaves the complementary target nucleic acid sequence in a site specific manner that is facilitated by the unwinding of the guide RNA targeting target nucleic acid sequence.

15. The eukaryotic cell of claim 14 wherein the eukaryotic cell is a yeast cell, a plant cell or a mammalian cell.

16. The eukaryotic cell of claim 14 wherein the eukaryotic cell is a human cell.

17. The eukaryotic cell of claim 14 wherein the cell further includes a plurality of nucleic acids encoding a plurality of guide DNA sequences complementary to different complementary target nucleic acid sequences.

18. The eukaryotic cell of claim 14 wherein the guide RNA targeting target nucleic acid sequence and the complementary target nucleic acid sequence are about 75 to 150 base pairs apart.

* * * * *